(12) United States Patent
Choi et al.

(10) Patent No.: US 9,709,505 B2
(45) Date of Patent: Jul. 18, 2017

(54) TURBIDITY SENSOR AND CONTROL METHOD THEREOF

(71) Applicant: SAMSUNG ELECTRONICS CO., LTD., Suwon (KR)

(72) Inventors: Jun Hoe Choi, Daejeon (KR); Byung Ik Choi, Pohang (KR); Jeong Su Han, Suwon (KR); Ji Hoon Ha, Suwon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 13/867,577

(22) Filed: Apr. 22, 2013

(65) Prior Publication Data
US 2013/0278921 A1    Oct. 24, 2013

(30) Foreign Application Priority Data

Apr. 23, 2012  (KR) .......................... 10-2012-0042327
Apr. 19, 2013  (KR) .......................... 10-2013-0043793

(51) Int. Cl.
*G01N 21/00* (2006.01)
*G01N 21/85* (2006.01)
(Continued)

(52) U.S. Cl.
CPC .......... *G01N 21/85* (2013.01); *A47L 15/4297* (2013.01); *D06F 33/02* (2013.01);
(Continued)

(58) Field of Classification Search
CPC .... G01N 21/53; G01N 21/51; G01N 15/1434; G01N 15/0205; G01N 15/1459
(Continued)

(56) References Cited

U.S. PATENT DOCUMENTS 5,083,447 A * 1/1992 Kiuchi ................. G01N 21/534
                                                     68/12.02
5,140,842 A * 8/1992 Kiuchi ................. D06F 39/004
                                                     68/12.02
(Continued)

FOREIGN PATENT DOCUMENTS

CN         1298978         6/2001
CN         1576823         2/2005
(Continued)

OTHER PUBLICATIONS

Extended European Search Report dated May 19, 2014 in corresponding European Patent Application No. 13164787.7.
(Continued)

*Primary Examiner* — Tarifur Chowdhury
*Assistant Examiner* — Md M Rahman
(74) *Attorney, Agent, or Firm* — Staas & Halsey LLP

(57) ABSTRACT

Disclosed herein are a turbidity sensor and a control method thereof, and more particularly, to a turbidity sensor capable of measuring turbidity of water including a liquid detergent as well as water including a powdered detergent and a control method thereof. The turbidity sensor includes a first light emitting unit emitting visible light, a first light receiving unit disposed opposite to the first light emitting unit at a position spaced apart from the first light emitting unit and receiving visible light emitted from the first light emitting unit, and a control unit determining a turbidity of a solution according to a ratio between the amount of visible light emitted from the first light emitting unit and the amount of visible light received by the first light receiving unit. According to the turbidity sensor and control method thereof, turbidity of the solution by the first and second particles is accurately measured.

15 Claims, 32 Drawing Sheets

(51) Int. Cl.
*A47L 15/42* (2006.01)
*D06F 39/00* (2006.01)
*G01N 21/53* (2006.01)
*D06F 39/08* (2006.01)
*D06F 33/02* (2006.01)
*D06F 35/00* (2006.01)

(52) U.S. Cl.
CPC .......... *D06F 35/006* (2013.01); *D06F 39/004* (2013.01); *D06F 39/08* (2013.01); *G01N 21/534* (2013.01); *D06F 2202/02* (2013.01); *D06F 2204/08* (2013.01)

(58) Field of Classification Search
USPC ........................................................ 356/338
See application file for complete search history.

(56) References Cited

U.S. PATENT DOCUMENTS

| | | | |
|---|---|---|---|
| 5,444,531 A | | 8/1995 | Foreman et al. |
| 6,723,554 B1* | | 4/2004 | Gaillon ................. G01N 21/03 |
| | | | 356/300 |
| 7,282,101 B2* | | 10/2007 | McCurdy ............. B01F 1/0005 |
| | | | 134/123 |
| 8,767,213 B2* | | 7/2014 | Pimputkar .......... A47L 15/4297 |
| | | | 250/573 |
| 2002/0159061 A1* | | 10/2002 | Ottens et al. ................. 356/338 |
| 2005/0190370 A1* | | 9/2005 | Ciobanu et al. .............. 356/442 |
| 2006/0152730 A1 | | 7/2006 | Schneider |
| 2006/0189862 A1* | | 8/2006 | Casciani ............ A61B 5/14542 |
| | | | 600/338 |
| 2006/0198761 A1* | | 9/2006 | Tokhtuev et al. .......... 422/82.05 |
| 2008/0040063 A1* | | 2/2008 | Curtius et al. ................ 702/104 |
| 2009/0231581 A1* | | 9/2009 | Han .................... A47L 15/4297 |
| | | | 356/341 |
| 2010/0195091 A1* | | 8/2010 | Fauth .................. A47L 15/4297 |
| | | | 356/51 |
| 2011/0273714 A1* | | 11/2011 | Pimputkar et al. ........... 356/442 |
| 2013/0230885 A1* | | 9/2013 | Jaeger .................. G01N 33/582 |
| | | | 435/69.1 |

FOREIGN PATENT DOCUMENTS

| | | |
|---|---|---|
| CN | 1918335 | 2/2007 |
| CN | 101532946 | 9/2009 |
| CN | 101961236 | 2/2011 |
| CN | 102224288 | 10/2011 |
| DE | 19937756 A1 | 2/2001 |
| DE | 102004057957 A1 | 6/2006 |
| DE | 102007016215 | 10/2007 |
| DE | 102006052892 A1 | 5/2008 |
| EP | 0992621 A2 | 4/2000 |
| EP | 0992621 A3 | 4/2000 |
| EP | 1245713 | 10/2002 |
| EP | 2182105 A1 | 5/2010 |
| EP | 2206457 A1 | 7/2010 |
| EP | 2221604 A1 | 8/2010 |
| JP | 6222689 | 1/1987 |
| JP | 2009-28113 | 2/2009 |
| JP | 2011050662 | 3/2011 |
| KR | 10-2009-0098453 | 9/2009 |
| KR | 10-2011-0086717 | 7/2011 |
| WO | 2005/119216 A1 | 12/2005 |

OTHER PUBLICATIONS

Office Action, dated Aug. 30, 2016, in Chinese Application No. 2013101440076 (19 pp.).
Sadar, et al., *Water Turbidity Precision Detection Technology*, Jun. 30, 2008, pp. 5-6 (3 pp.).
Lun, et al., *Inspection and Maintenance of the Instrument*, Jun. 30, 2011, p. 142.
Chinese Office Action dated Mar. 20, 2017 in corresponding Chinese Patent Application No. 201310144007.6.

* cited by examiner

TURBIDITY SENSOR AND CONTROL METHOD THEREOF

CROSS-REFERENCE TO RELATED APPLICATIONS

This application claims the benefit of Korean Patent Application No. 10-2012-0042327 and 10-2013-0043793, filed on Apr. 23, 2012 and Apr. 19, 2013, respectively, in the Korean Intellectual Property Office, the disclosure of which is incorporated herein by reference.

BACKGROUND

1. Field

Embodiments of the present disclosure relate to a turbidity sensor capable of measuring turbidity of an aqueous solution including a liquid detergent as well as an aqueous solution including a powdered detergent and a control method thereof.

2. Description of the Related Art

Some of electric home appliances using water, such as washing machines and dishwashers, have a turbidity sensor to measure turbidity and change a washing operation according to the sensed turbidity. These electric home appliances change number of a washing operation according to the turbidity sensed by the turbidity sensor, thereby reducing waste of water and carrying out an optimal washing operation.

As illustrated in FIGS. 1A and 1B, a turbidity sensor 3 includes one light emitting unit 3a emitting light and one light receiving unit 3b receiving the light emitted from the light emitting unit 3a to measure turbidity of water using intensity of light emitted from the light emitting unit 3a and the intensity of the light received by the light receiving unit 3b.

That is, when the light emitting unit 3a emits light at a predetermined intensity, the light receiving unit receives light that is not scattered by particles floating in water to measure turbidity of water. Here, the measured turbidity (F) may be obtained as an output of a function represented by Equation 1 below.

$$F \text{ (turbidity)} = a \times (\text{amount of light received by light receiving unit/amount of light emitted from light emitting unit}) \quad \text{Equation 1}$$

In Equation 1, a is a proportional constant. As the turbidity of the water increases, the amount of light received by the light receiving unit 3b becomes smaller than that emitted from the light emitting unit 3a. Thus, the obtained output of Equation 1 decreases.

When the turbidity of water is high, as shown in FIG. 1A, a large amount of light emitted from the light emitting unit 3a is scattered by particles contained in the water, and only a small amount of the light is received by the light receiving unit 3b, and thus the obtained output of Equation 1 decreases. On the other hand, when the turbidity of the water is low, as shown in FIG. 1B, a large amount of the light emitted from the light emitting unit 3a passes through the water and is received by the light receiving unit 3b and thus the obtained output value of Equation 1 increases. FIG. 2 shows output of the turbidity sensor 3 with respect to turbidity of water.

As shown in FIG. 2, as turbidity decreases (C), output of the turbidity sensor 3 increases. On the other hand, as turbidity increases (D), output of the turbidity sensor 3 decreases.

When a powdered detergent is used, outputs of such a conventional turbidity sensor 3, which determines turbidity using light having a wavelength in an infrared range, are accurately distinguishable according to the amount of the powdered detergent and pollution level of water since the particle size of the powdered detergent is large enough.

However, when a liquid detergent is used, outputs of the turbidity sensor 3 are not distinguishable according to the amount of the liquid detergent in comparison with pure water due to a small particle size of the liquid detergent.

SUMMARY

Therefore, it is an aspect of the present disclosure to provide a turbidity sensor and a control method thereof.

Additional aspects will be set forth in part in the description which follows and, in part, will be obvious from the description, or may be learned by practice of the invention.

In accordance with one aspect, a turbidity sensor includes a first light emitting unit emitting visible light, a first light receiving unit disposed opposite to the first light emitting unit at a position spaced apart from the first light emitting unit and receiving visible light emitted from the first light emitting unit, and a control unit determining a turbidity of a solution according to a ratio between the amount of visible light emitted from the first light emitting unit and the amount of visible light received by the first light receiving unit.

The first light emitting unit may further emit infrared light, the turbidity sensor may further include a second light receiving unit disposed opposite to the first light emitting unit at a position spaced apart from the first light emitting unit and receiving infrared light emitted from the first light emitting unit, and the control unit may determine a turbidity of the solution measured using visible light according to a ratio between the amount of visible light emitted from the first light emitting unit and the amount of visible light received by the first light receiving unit and determines a turbidity of the solution measured using infrared light according to a ratio between the amount of infrared light emitted from the first light emitting unit and the amount of infrared light received by the second light receiving unit.

The turbidity sensor may further include a second light emitting unit emitting infrared light and a second light receiving unit disposed opposite to the second light emitting unit at a position spaced apart from the second light emitting unit and receiving infrared light emitted from the second light emitting unit, and the control unit may determine a turbidity of the solution measured using visible light according to a ratio between the amount of visible light emitted from the first light emitting unit and the amount of visible light received by the first light receiving unit and determines a turbidity of the solution measured using infrared light according to a ratio between the amount of infrared light emitted from the second light emitting unit and the amount of infrared light received by the second light receiving unit.

The first light emitting unit may further emit infrared light, the first light receiving unit may further receive infrared light emitted from the first light emitting unit, and the control unit may determine a turbidity of the solution measured using visible light according to a ratio between the amount of visible light emitted from the first light emitting unit and the amount of visible light received by the first light receiving unit and determines a turbidity of the solution measured using infrared light according to a ratio between the amount of infrared light emitted from the first light emitting unit and the amount of infrared light received by the first light receiving unit.

The turbidity sensor further may include a second light emitting unit emitting infrared light, the first light receiving unit may further receives infrared light emitted from the second light emitting unit, and the control unit may determine a turbidity of the solution measured using visible light according to a ratio between the amount of visible light emitted from the first light emitting unit and the amount of visible light received by the first light receiving unit and determines a turbidity of the solution measured using infrared light according to a ratio between the amount of infrared light emitted from the second light emitting unit and the amount of infrared light received by the first light receiving unit.

The first light receiving unit may be a multilayer photo diode including a visible light receiving unit including a vertical PN junction and an infrared light receiving unit including a vertical PN junction, and wavelength ranges may be adjusted by controlling concentrations of impurities constituting each of the PN junctions The first light receiving unit may be a multilayer photo diode including a visible light receiving unit including a vertical PN junction and an infrared light receiving unit including a vertical PN junction, and wavelength ranges may be adjusted by controlling concentrations of impurities constituting each of the PN junctions.

The first light receiving unit may be a multilayer photo diode including a visible light receiving unit including a horizontal PN junction and an infrared light receiving unit including a horizontal PN junction, and wavelength ranges may be adjusted by controlling concentrations of impurities constituting each of the PN junctions.

The first light receiving unit may be a multilayer photo diode including a visible light receiving unit including a horizontal PN junction and an infrared light receiving unit including a horizontal PN junction and wavelength ranges may be adjusted by controlling concentrations of impurities constituting each of the PN junctions The ratio may be obtained by the amount of visible light received by the first light receiving unit/the amount of visible light emitted from the first light emitting unit.

The turbidity sensor may further include a light emitting unit case allowing light emitted from the first light emitting unit to travel straight to the first light receiving unit, and a light receiving unit case allowing light emitted from the first light emitting unit to be incident upon the first light receiving unit and blocking scattered light.

The turbidity sensor may further include a light emitting unit cover surrounding the first light emitting unit to prevent the first light emitting unit from directly contacting the solution, and a light receiving unit cover surrounding the first light receiving unit to prevent the first light receiving unit from directly contacting the solution.

When a turbidity measured using visible light is greater than a first reference value and a turbidity measured using infrared light is greater than a second reference value, the sensor control unit may determine that both of first and second particles are contained in the solution, determine that a detergent contained in the solution is a powdered detergent, and determine a turbidity of the solution based on the turbidity of the solution measured using infrared light.

When a turbidity measured using visible light is greater than a first reference value and a turbidity measured using infrared light is less than a second reference value, the sensor control unit may determine that second particles are contained in the solution, determine that a detergent contained in the solution is a liquid detergent, and determine a turbidity of the solution based on the turbidity of the solution measured using visible light.

When a turbidity measured using visible light is less than a first reference value, the sensor control unit may determine that the solution is clean.

In accordance with one aspect, a method of controlling a turbidity sensor includes emitting visible light, receiving visible light, and determining a turbidity of a solution measured using visible light according to a ratio between the amount of emitted visible light and the amount of received visible light.

The emitting of visible light may further include emitting infrared light, the receiving of visible light may further include receiving infrared light, and the determining may include determining a turbidity of the solution measured using visible light according to a ratio between the amount of emitted visible light and the amount of received visible light, and determining a turbidity of the solution measured using infrared light according to a ratio between the amount of emitted infrared light and the amount of received infrared light.

When a turbidity of the solution measured using visible light is greater than a first reference value, and a turbidity of the solution measured using infrared light is greater than a second reference value, the determining may conclude that both of first and second particles are contained in the solution, conclude that a detergent contained in the solution is a powdered detergent, and judge a turbidity of the solution based on the turbidity of the solution measured using infrared light When a turbidity of the solution measured using visible light is greater than a first reference value, and a turbidity of the solution measured using infrared light is less than a second reference value, the determining may conclude that second particles are contained in the solution, conclude that a detergent contained in the solution is a liquid detergent, and judge a turbidity of the solution based on the turbidity of the solution measured using visible light.

When a turbidity of the solution measured using visible light is less than a first reference value, the determining may conclude that the solution is clean.

According to the turbidity sensor and the control method thereof according embodiments of the present invention, turbidity of an aqueous solution by the liquid detergent may be accurately measured.

In addition, according to the turbidity sensor and the control method thereof according embodiments, turbidity of an aqueous solution according to first particles and second particles may be accurately measured.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1A:
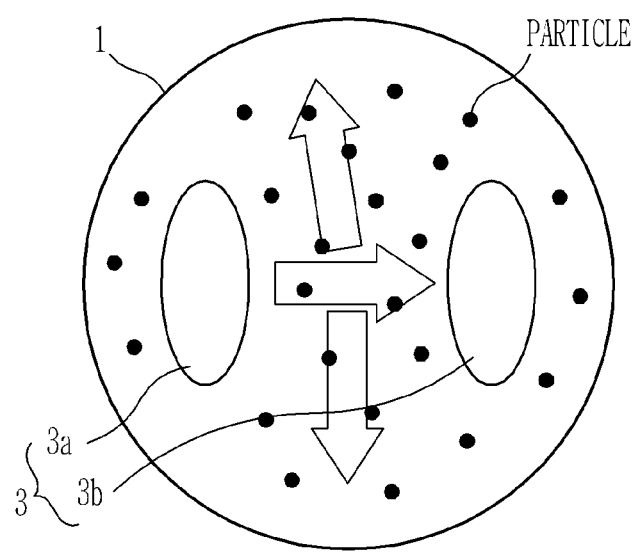
FIG. 1A is a conceptual view illustrating a turbidity sensor, in the case that turbidity is high.
Figure 1B:
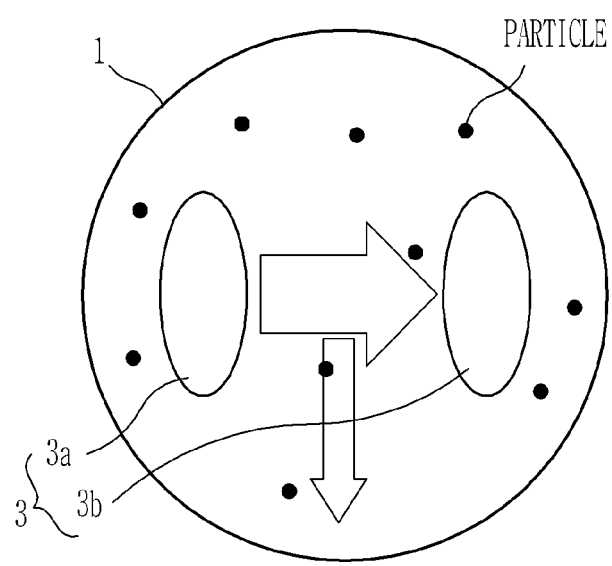
FIG. 1B is a conceptual view illustrating the turbidity sensor, in the case that turbidity is low.
Figure 2:
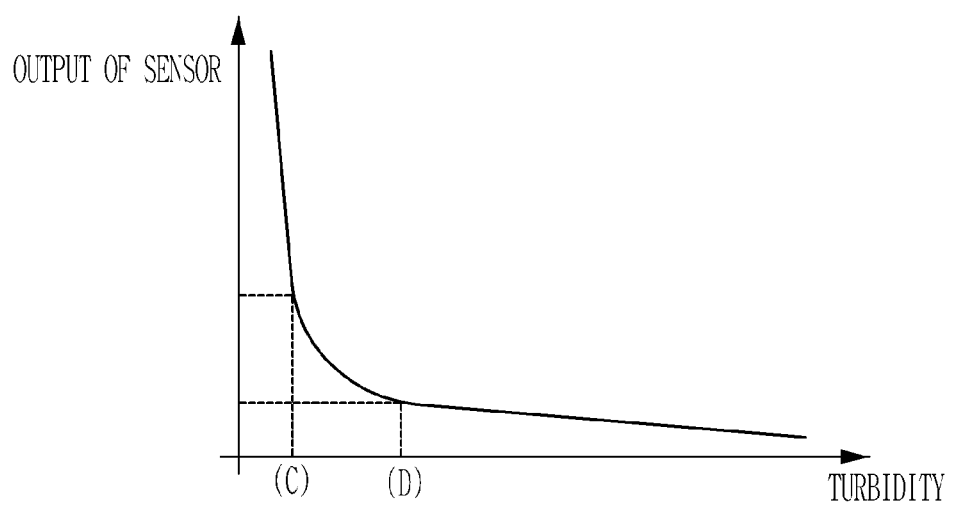
FIG. 2 is a graph illustrating output waveform of the turbidity sensor.

Reference will now be made in detail to the embodiments, examples of which are illustrated in the accompanying drawings, wherein like reference numerals refer to like elements throughout.

Hereinafter, terms used in the following description will be briefly described.

Particles are classified into first particles and second particles. When a powdered detergent is dissolved in water, first particles having a relatively great particle size and second particles having a relatively small particle size are formed in the water by the powdered detergent. The first particles may be sensed by infrared light and may have a particle diameter of several micrometers (μm) to hundreds of micrometers (μm). The second particles may be sensed by visible light and may have a particle diameter of several nanometers (nm) to hundreds of nanometers (nm). The particle size ranges of the first and second particles may vary and overlap each other. In addition, when a liquid detergent is dissolved in water, second particles having a relatively small particle size are formed in the water by the liquid detergent. The second particles may be sensed by visible light and may have a particle diameter of several nanometers (nm) to hundreds of nanometers (nm). The particles size ranges of the second particles may vary.

In addition, a tub, a container, and a washing tub used herein may have a similar concept. In addition, a solution may be described as a similar concept to water. Also, turbidity may be described as a similar concept to pollution level. Vague expressions may be correctly understood in accordance with the context.

Figure 3A:
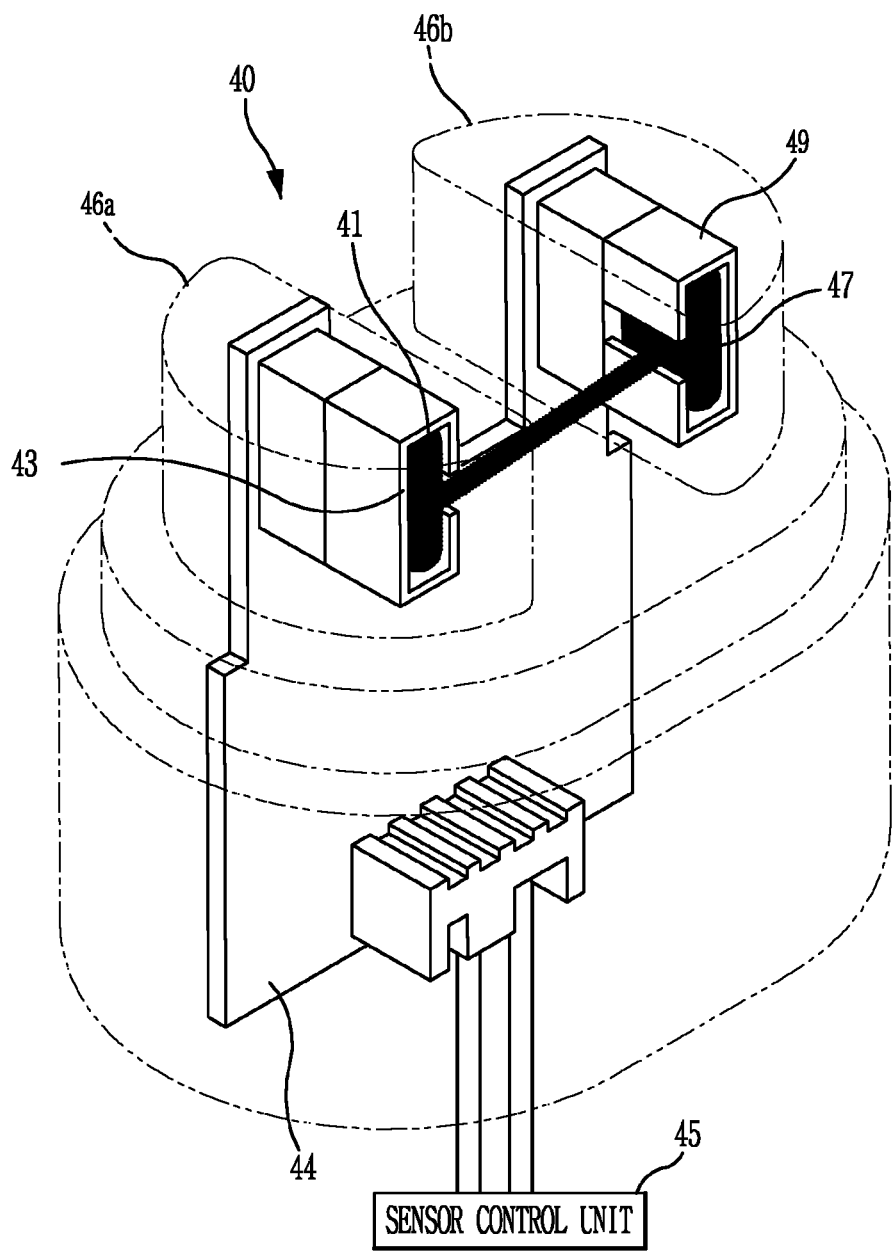
FIG. 3A is a view illustrating an example of a turbidity sensor according to an embodiment.
Figure 3B:
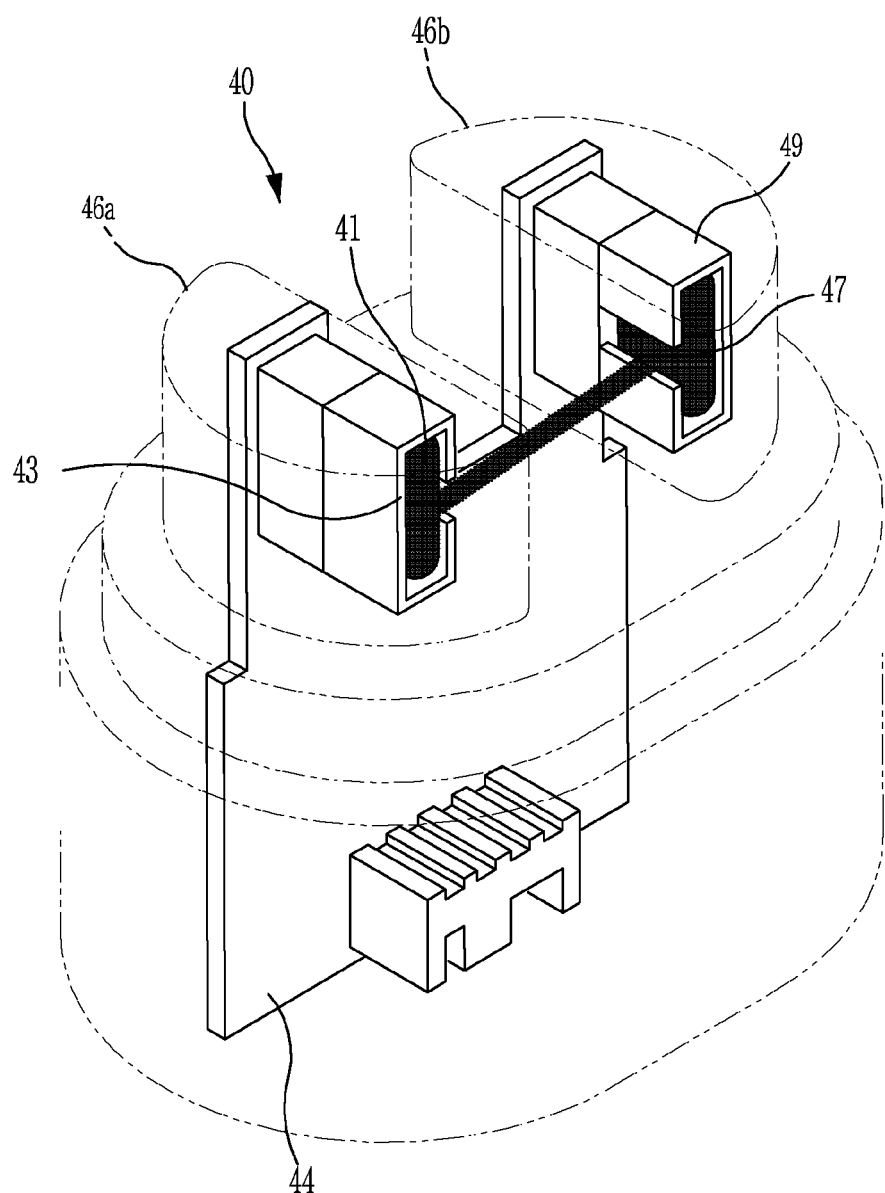
FIG. 3B is a view illustrating another example of a turbidity sensor according to an embodiment.

FIG. 3A is a view illustrating an example of a turbidity sensor 40 according to an embodiment. FIG. 3B is a view illustrating another example of a turbidity sensor 40.

Referring to FIG. 3A, the turbidity sensor 40 includes a cover 46 forming the external appearance of the turbidity sensor 40 while covering the turbidity sensor 40 to prevent the turbidity sensor 40 from making direct contact with water, a first light emitting unit 41 emitting visible light, a first light receiving unit 47 receiving light emitted from the first light emitting unit 41, and a substrate 44 installed at an inside the cover 46 in perpendicular to the cover 46 to fix the first light emitting unit 41 and the first light receiving unit 47 that are mounted on the substrate 44.

A light emitting device, such as a light emitting diode, may be used as the first light emitting unit 41, and a light receiving device, such as a photo transistor and a photodiode, may be used as the first light receiving unit 47.

The first light emitting unit 41 may be disposed in a light emitting unit case 43 having a structure in which light travels straight in a narrow range. The first light receiving unit 47 may be disposed opposite to the first light emitting unit 41 so as to be located within a straight traveling path of light emitted from the first light emitting unit 41. The light emitting unit case 43 configured such that light travels straight in a narrow range and a light receiving unit case 49 configured such that light is received by the first light receiving unit 47 may also have other structures as long as they perform the same function.

In addition, the turbidity sensor 40 may further include a sensor control unit 45, which receives the amount of light emitted from the first light emitting unit 41 and the amount of light received by the first light receiving unit 47, calculates a ratio of the amounts, determines turbidity of water using the ratio of the amounts of light, and determines the amount of particles. The particles may include first particles or second particles.

Thus, when the first light emitting unit 41 emits visible light at a uniform intensity, the first light receiving unit 47 receives light, which passes through water in a container 30 and travels straight. Then, the sensor control unit 45 receives the amount of light received by the first light receiving unit 47 and calculates a ratio of the amounts of the light, thereby measuring turbidity of water. In this regard, the measured turbidity (F) may be obtained as an output of a function represented by Equation 2 below.

$$F \text{ (turbidity)} = a \times (\text{amount of visible light received by light receiving unit/amount of visible light emitted from light emitting unit}) \quad \text{Equation 2}$$

In Equation 2, a is a proportional constant. The amount of visible light emitted from the light emitting unit refers to a voltage measured by the light receiving unit when visible light emitted from the light emitting unit is incident upon the light receiving unit without encountering an obstacle in the path thereof, and the amount of visible light received by the light receiving unit refers to a voltage measured by the light receiving unit when visible light emitted from the light emitting unit is incident upon the light receiving unit after partially scattered while passing through a solution or the like. This may be applied to infrared light in the same manner.

As turbidity of water increases, the amount of light received by the first light receiving unit 47 become much smaller than the amount of light emitted from the first light emitting unit 41. As a result, the output value of Equation 2 decreases. In Equation 2, the light emitting unit may include a first light emitting unit or a second light emitting unit, and the light receiving unit may include a first light receiving unit or a second light receiving unit.

As illustrated in FIG. 3B, the turbidity sensor 40 according to the embodiment illustrated in FIG. 3A may have a structure not including the sensor control unit 45. In this case, the function of the sensor control unit 45 may be performed by a device including the turbidity sensor 40.

Figure 3C:
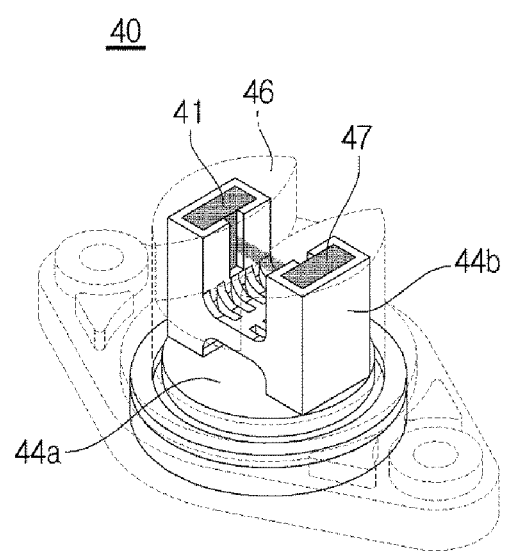
FIG. 3C is a view illustrating still another example of a turbidity sensor according to an embodiment.

FIG. 3C is a view illustrating still another example of a turbidity sensor according to an embodiment. The description of the same reference numerals will be assigned to the elements according to the present invention identical to the elements according to the previous embodiment. The details of elements identical to those of the previous embodiment will be omitted in order to avoid redundancy.

Referring to FIG. 3C, the turbidity sensor 40 includes a cover 46 forming the external appearance of the turbidity sensor 40, a substrate 44a installed at an inside the cover 46 in parallel to the cover 46, a first light emitting unit 41 emitting light of a visible light, a light receiving unit 47 receiving the light being emitted from the first light emitting unit 41, and a U-shaped case 44b installed on the substrate 44a to fix the first light emitting unit 41 and the first light receiving unit 47 that are installed on the U-shaped case 44b.

The first light emitting unit 41 outputs a predetermined amount of light that is determined by a control signal that is being input, and the first light receiving unit 46 outputs a predetermined magnitude of electric signal that is determined by the amount of light being received. In detail, the first light receiving unit 47 outputs an electric signal having a great magnitude at a clean water not containing contamination materials, and outputs an electric signal having a small magnitude when the turbidity is increased.

In addition, the first light receiving unit 47 outputs an electric signal having a predetermine magnitude that is determined according to the amount of light being received. Accordingly, in order to maintain the sensitivity at a predetermined level or above even if the sensitivity of the first receiving unit 47 is lowered due to a change with the passage of time, a calibration needs to be performed such that the first light receiving unit 47 outputs a maximum magnitude of electric signal in the clean water not containing contamination materials.

The calibration of the first light receiving unit 47 may be performed by measuring the electric signal, which is output from the first light receiving unit 47, at the clean water not containing the contamination materials while adjusting the control signal being input to the first light emitting unit 41. That is, the turbidity sensor 40 may determine, as a reference value, a control signal being input to the first light emitting unit 41 when the electric signal being output from the first light receiving unit 47 has the maximum magnitude.

As the calibration of the first light receiving unit 47 is performed as described above, the sensitivity of the turbidity sensor 40 is improved.

Figure 4A:
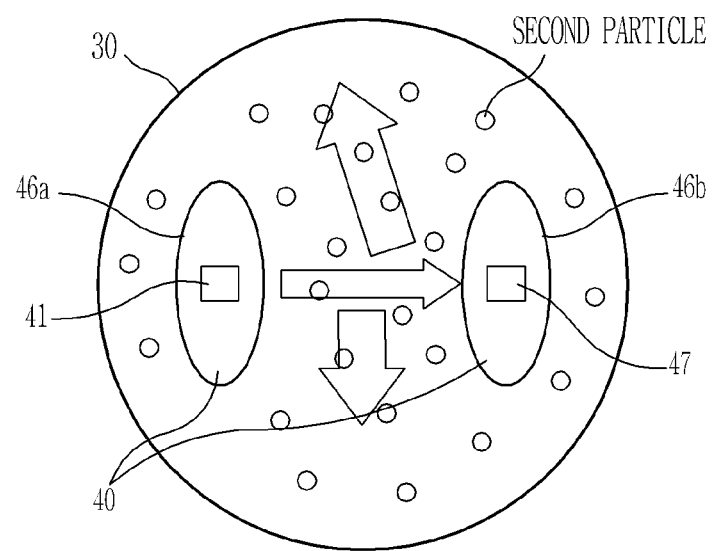
FIG. 4A is a conceptual view illustrating the turbidity sensor according to the embodiment illustrated in FIG. 3A, in the case that turbidity is high.
Figure 4B:
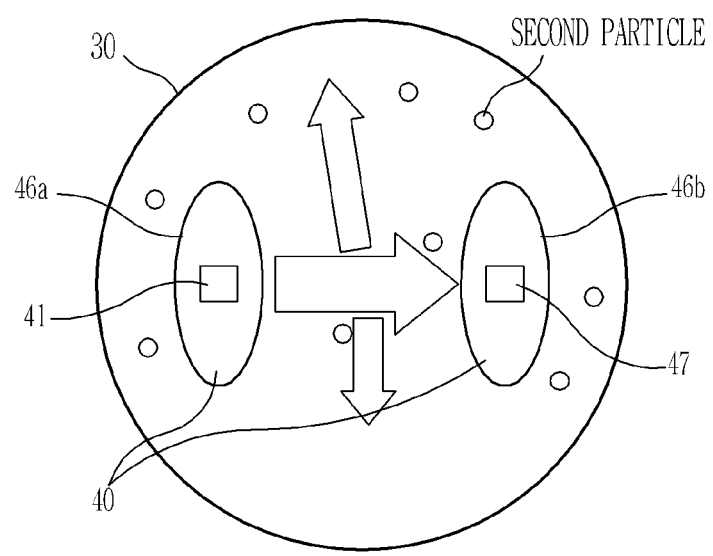
FIG. 4B is a conceptual view illustrating the turbidity sensor according to the embodiment illustrated in FIG. 3A, in the case that turbidity is low.

FIG. 4A is a conceptual view illustrating the turbidity sensor according to the embodiment illustrated in FIG. 3A, in the case that turbidity is high. FIG. 4B is a conceptual view illustrating the turbidity sensor according to the embodiment illustrated in FIG. 3A, in the case that turbidity is low.

When the turbidity of water in the container 30 is high as illustrated in FIG. 4A, the amount of light scattered by particles contained in the water is larger than that amount of light traveling straight, and thus the amount of light received by the first light receiving unit 47 decreases.

On the other hand, when the turbidity of water in the container 30 is low as illustrated in FIG. 4B, the amount of light scattered by particles in the water is less than that amount of light traveling straight, and thus the amount of light received by the first light receiving unit 47 increases.

Thus, when the turbidity is high as shown in FIG. 4A, a large amount of visible light emitted from the first light emitting unit 41 is scattered by particles contained in the water, and only a small amount among the light is received by the first light receiving unit 47, and thus the obtained output of the turbidity sensor 40 decreases. When the turbidity is low as shown in FIG. 4B, a large amount of visible light emitted from the first light emitting unit 41 passes through the water and is received by the first light receiving unit 47, and thus the obtained output of the turbidity sensor 40 increases.

Figure 5:
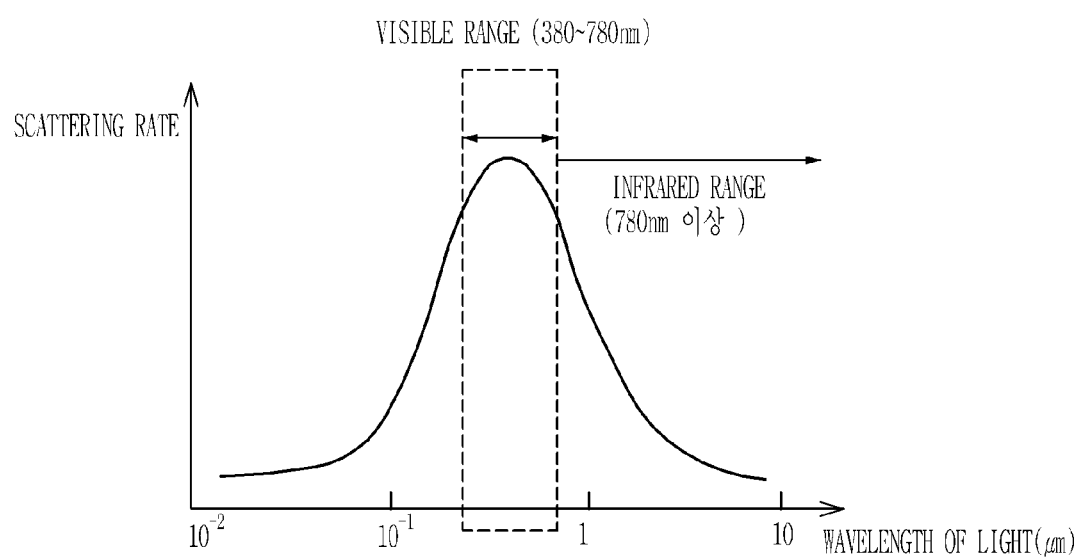
FIG. 5 is a graph illustrating scattering rate of light with respect to wavelength of light according to the embodiment illustrated in FIG. 3A.

FIG. 5 is a graph illustrating scattering rate of light with respect to wavelength of light according to the embodiment illustrated in FIG. 3A.

Referring to FIG. 5, the scattering rate is high in a relatively short wavelength range such as a visible light range, and the light scattering rate is low in a relatively long wavelength range such as an infrared light range. Based on the principle that the sensitivity is low in infrared light due to a low scattering rate and the sensitivity is high in visible light due to a high scattering, the second particles having a smaller particle size than the first particles may be sensed when the first light emitting unit 41 emits visible light and the first light receiving unit 47 receives visible light. As such, when visible light used, the amount of light received by the first light receiving unit 47 may be considerably reduced by increasing the light scattering rate according to the amount of the second particles.

Figure 6A:
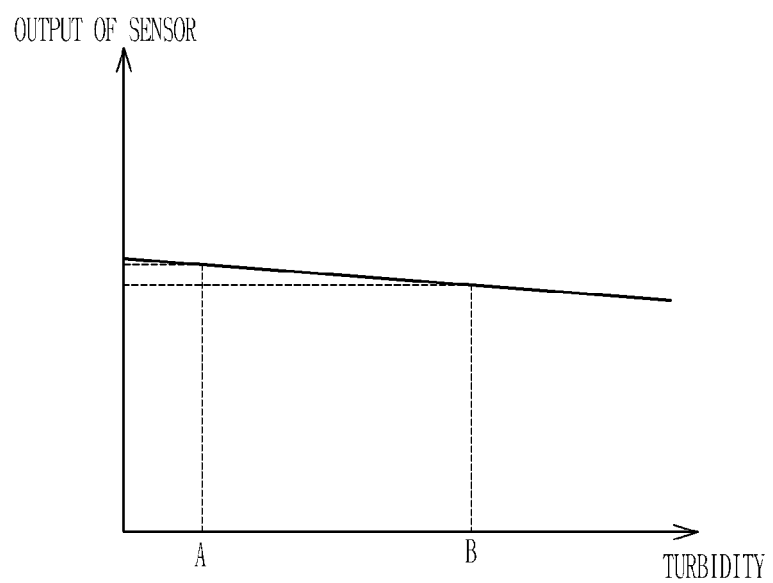
FIG. 6A is a graph illustrating output of the turbidity sensor with respect to turbidity in a solution containing second particles when infrared light is emitted thereto.

FIG. 6A is a graph illustrating output of the turbidity sensor with respect to turbidity in a solution containing second particles when infrared light is emitted thereto.

Since the first particles have a sufficiently large particle size, the turbidity sensor 40 may accurately distinguish the output of the turbidity sensor according to the amount of the first particles using infrared light.

However, as illustrated in FIG. 6A, since the second particles have a small particle size, the output of the turbidity sensor obtained from water containing a large amount of the second particles is not distinguishable from that obtained from pure water using infrared light.

Figure 6B:
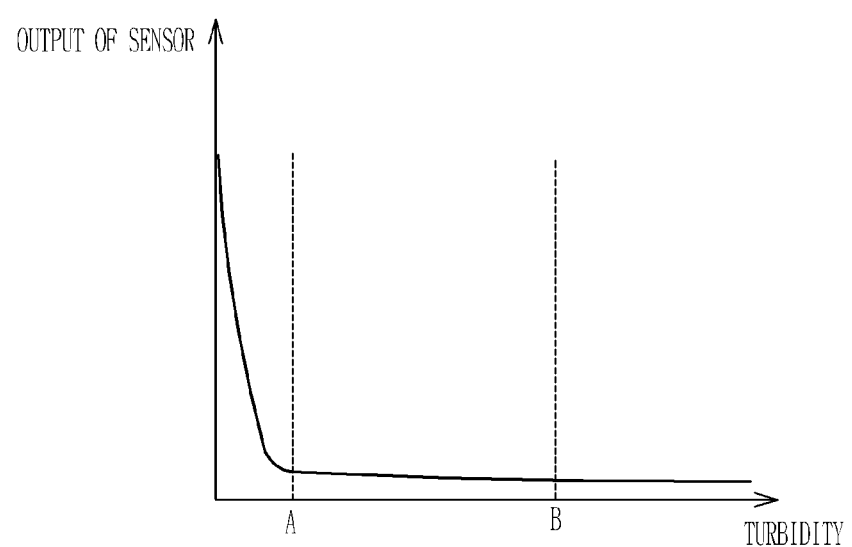
FIG. 6B is a graph illustrating output of the turbidity sensor with respect to turbidity in a solution containing first particles when visible light is emitted thereto.

FIG. 6B is a graph illustrating output of the turbidity sensor with respect to turbidity in a solution containing first particles when visible light is emitted thereto.

When visible light is used, the amount of light received by the first light receiving unit 47 may be considerably reduced since the light scattering rate also increases by the second particles having a relatively small particle size compared to the first particles.

However, since the first particles have a relatively larger particle size than the second particles, a very small amount of the first particles may also increase the light scattering rate when visible light is used, thereby reducing the amount of light received by the first light receiving unit 47.

Thus, infrared light may be used to sense the first particles, and visible light may be used to sense the second particles.

Figure 6C:
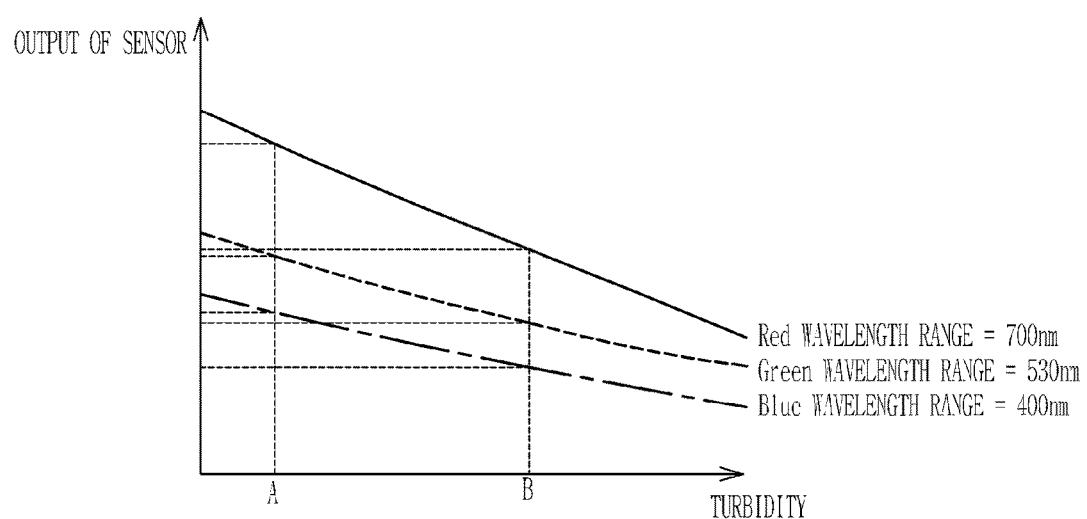
FIG. 6C is a graph illustrating output of the turbidity sensor with respect to turbidity by second particles according to wavelength of visible light according to the embodiment illustrated in FIG. 3A.

FIG. 6C is a graph illustrating output of the turbidity sensor 40 with respect to turbidity by second particles according to wavelength of visible light according to the embodiment illustrated in FIG. 3A.

FIG. 6C shows outputs of the turbidity sensor 40 according to the degree of pollution using visible light. Since the scattering rate of visible light by the second particles having a relatively small particle size is also high, the output of the turbidity sensor 40 in case that turbidity is low (A) is significantly different from that of the turbidity sensor 40 in case that turbidity is high (B). Accordingly, turbidity may be accurately determined, and thus the amount of the second particles may also be accurately detected.

In addition, visible light exhibits various scattering rates according to wavelength thereof.

Thus, in order to determine turbidity caused by the second particles, visible light may be used. When visible light is used, not only turbidity caused by not only the second particles but also by the first particles may be detected.

The relation between light scattering principle and the particle size of a material is shown in Table 1 below.

TABLE 1

| Type of particle | Property | Wavelength to detect turbidity |
|---|---|---|
| First particle | large particle size | infrared light |
| Second particle | small particle size | visible light |

Referring to Table 1, as the particle size increases, light with a longer wavelength is suitable for detecting the amount of the particles. As the particle size decreases, light with a shorter wavelength is suitable for detecting the amount of the particles.

Thus, in order to detect the second particles, the first light emitting unit 41 may emit visible light and the first light receiving unit 47 may receive the visible light emitted from the first light emitting unit 41. The sensor control unit 45 according to the embodiment illustrated in FIG. 3A may determine turbidity of a solution measured using visible light by use of the amount of visible light emitted from the first light emitting unit 41 and the amount of visible light received by the first light receiving unit 47.

In addition, all the turbidities provided by the first particle and the second particle, respectively, may be detected by selecting an appropriated wavelength of light and an appropriate detecting distance.

When assumed that the amount of the first particles is the same as the second particles, the first particles cause a relatively large turbidity and the second particles cause a relatively small turbidity. That is, the first particle has a size of several micrometers (μm) to hundreds of micrometers (μm), thereby causing a turbidity of hundreds of NTU (Nepthelometric Turbidity Unit) to thousands of NTU. The second particle has a size of several nanometers (nm) to hundreds of nanometers (nm), thereby causing a turbidity of several tens of NTU to hundreds of NTU.

As described above, since the ranges of the turbidities caused by the second particle and the second particle differ, the turbidity sensor 40 may detect all the turbidities provided the first particle and the second particle, respectively, by having the change of the electric signal, which is output from the first light receiving unit according to the change of the turbidity, varied according to the turbidity ranges.

In addition, in a low turbidity range, the sensitivity of the turbidity sensor 40 is adjusted to be relatively large, and in a high turbidity range, the sensitivity of the turbidity sensor 40 is adjusted to relatively small, so that the turbidity caused by the second particle in the low turbidity range is precisely detected, and the turbidity caused by the first particle in the high turbidity range is measured in a wider range. For example, in a turbidity range of hundreds of NTU, the output of the turbidity sensor 40 according to the change of the turbidity is adjusted to be relatively large, and in a turbidity range of hundreds of NTU to thousands of NTU, the output of the turbidity sensor 40 according to the change of the turbidity is adjusted to be relatively small, all the turbidities caused by the first particle and the second particle may be detected at an appropriate sensitivity.

Such a sensitivity of the turbidity sensor 40 with respect to the turbidity may vary with wavelengths of light being emitted from the first light emitting unit and the distance d between the first light emitting unit 41 and the first light receiving unit 47.

Figure 7A:
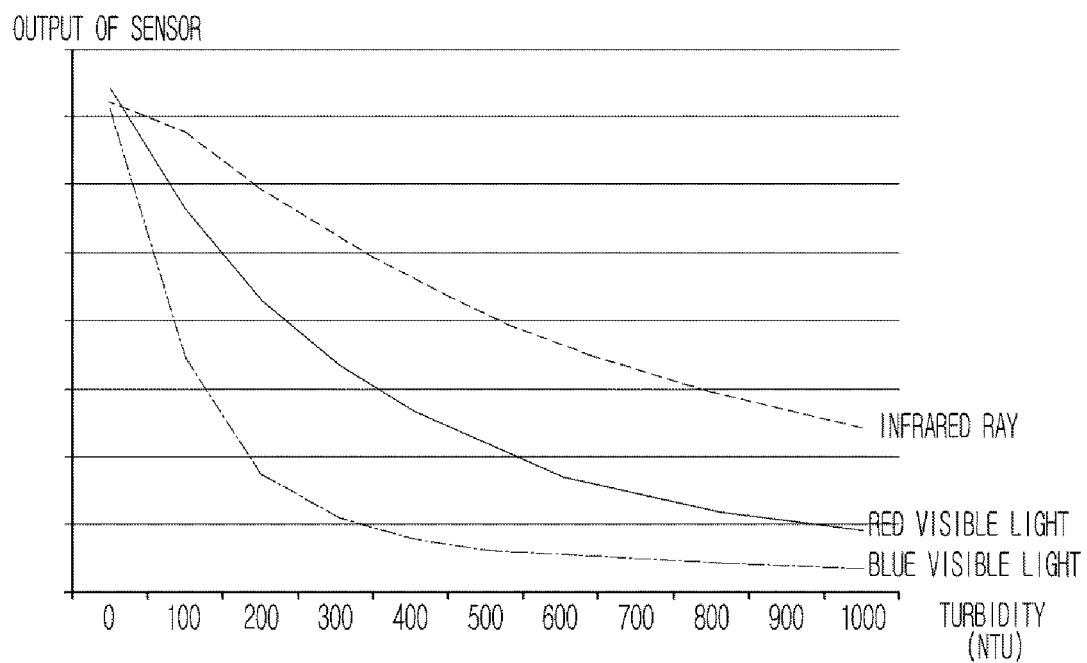
FIG. 7A is a view illustrating output of turbidity sensor with respect to the turbidity according to wavelength of light emitted by a first light emitting unit according to an embodiment.

FIG. 7A is a view illustrating output of turbidity sensor with respect to the turbidity according to the wavelength of light emitted by the first light emitting unit according to an embodiment. In detail, FIG. 7A shows an output of the first light receiving unit with respect to the turbidity when the distance d between the first light emitting unit 41 and the light receiving unit 47 is 21 mm, and the first light emitting unit 41 emits infrared ray having a wavelength of 940 nm, red visible light having a wavelength of 640 nm, and blue visible light having a wavelength of 460 nm. In FIG. 7A, the distance between the first light emitting unit 41 and the first light receiving unit 47 is randomly selected to find the tendency of change of the sensitivity according to the light being emitted from the first light emitting unit 41, and the present invention is not limited thereto. In addition, the wavelengths of 940 nm, 640 nm and 460 nm are selected from an infrared ray wavelength range, a red visible light wavelength range, and a blue visible light wavelength range, respectively, and the present invention is not limited thereto.

Referring to FIG. 7A, in a case in which the first light emitting unit 51 emits light of an infrared ray range, the magnitude of the electric signal being output from the first light receiving unit 47 is shown as being slowly decreased with the increase of the turbidity. Accordingly, in a case in which the first light emitting unit 41 emits light of the infrared range, the turbidity sensor 40 may detect a wide range of turbidity, but produces a low sensitivity in a turbidity range of about 300 NTU or below. That is, in a case in which the first light emitting unit 41 emits light of the infrared ray range, the turbidity is detected up to the range of thousands of NTU so the turbidity caused by the first particles may sufficiently detect. However, in a turbidity range of about 300 NTU or below, since the output signal of the first light receiving unit 47 according to the change of turbidity is small, the turbidity sensor 40 produces a low sensitivity with respect to the turbidity caused by the second particles.

In a case in which the first light emitting unit 41 emits light of the red visible light range, the variation of electric signal being output from the first light receiving unit 47 differ depending on the turbidity range. That is, in a turbidity range of 300 NTU or below, since the variation of the electric signal being output from the first light receiving unit 47 according to the change of the turbidity is relatively large, the turbidity sensor 40 has a high sensitivity, and in a turbidity range of 300 NTU or above, the variation of the electric signal being output for the first light receiving unit 47 according to the change of the turbidity is small, so a wide range of turbidity is detected. Accordingly, in a case in which the first light emitting unit 41 emits light of the red visible light range, the turbidity sensor 40 has a higher sensitivity for the second particles when compared to the case of infrared ray, and detects the turbidity up to the range of 1000 NTU or above for the first particles.

In a case in which the first light emitting unit 41 emits light of blue visible light range, the variation of the electric signal being output from the first light receiving unit 47 significantly differs depending on the turbidity range. That is, in a turbidity range of 300 NTU or below, since the variation of the electric signal being output from the first light receiving unit 47 according to the change of the turbidity is significantly large, the turbidity sensor 40 has a significantly high sensitivity, and in a turbidity range of 300 NTU or above, the variation of the electric signal being output from the first light receiving unit 47 according to the change of the change of the turbidity is small, and the output of the first light receiving unit 47 in the range of 1000 NTU almost becomes "0".

As described above, the sensitivity and the detection range of the turbidity sensor 40 vary according to the wavelength of light output from the first light emitting unit 41. That is, an appropriate wavelength of light may be selected according to a product to which the turbidity sensor 40 is applied.

For example, in a case of a washing machine, a liquid detergent is widely used as well as a powdery detergent. In a case in which the powdery detergent is used, the first particle is a primary contamination source, and causes a contamination of about 1000 NTU. In a case in which the liquid detergent is used, the second particle is a primary contamination source, and causes a contamination of about 300 NTU. That is, the washing machine is required to be sensitive to the turbidity caused by the second particle while having a detecting range up to 1000 NTU. Accordingly, in a case of a washing machine, the first light emitting unit 41 is desired to emit light of a blue visible light range.The sensitivity to turbidity and the detecting range according to the wavelength of light being output from the first light emitting unit 41 have been described above. Hereinafter, when light of the blue visible light range is emitted, the sensitivity to turbidity and the detecting range of turbidity according to the distance between the first light emitting unit 41 and the first light receiving unit 47, that is, the detecting distance will be described.

Figure 7B:
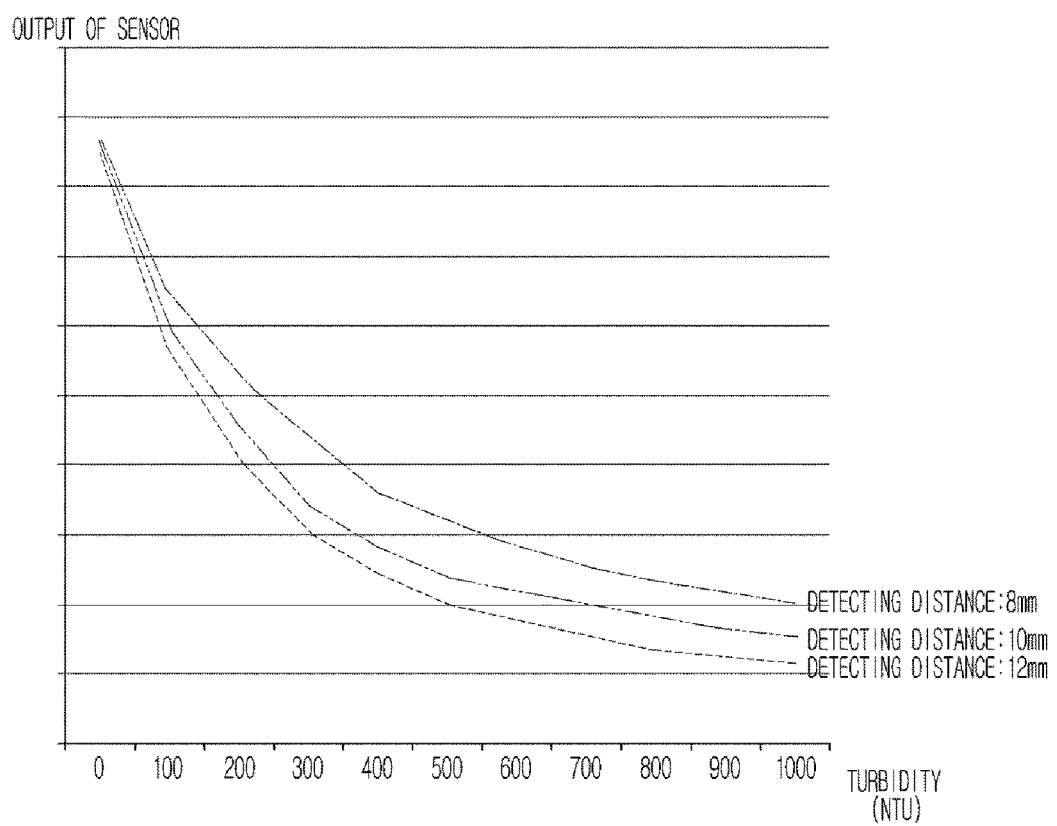
FIG. 7B is a view illustrating output of turbidity sensor with respect to the turbidity according to detecting distance of the turbidity sensor according to an embodiment.

FIG. 7B is a view illustrating output of turbidity sensor with respect to the turbidity according to the detecting distance of the turbidity sensor according to an embodiment. In detail, FIG. 7B shows the magnitude of the output signal of the first light receiving unit 47 according to the turbidity when the first light emitting unit 47 emits light of the blue visible light range and the detecting distances of the turbidity sensor 40 are 8 mm, 10 mm and 12 mm, respectively.

Referring to FIG. 7B, as the detecting distance of the turbidity sensor 40 is increased, the output signal of the first light receiving unit 47 is rapidly decreased. That is, when compared to the turbidity sensor 40 with a detecting distance of 8 mm, the first light receiving unit 47 with a detecting distance of 10 mm has an output signal more rapidly decreased with the increase of turbidity. In addition, when compared to the turbidity sensor 40 with a detecting distance of 10 mm, the first light receiving unit 47 with a detecting distance of 12 mm has an output signal more rapidly decreased with the increase of turbidity.

Accordingly, the sensitivity of the turbidity sensor 40 is improved with the increase of the detecting distance. However, as the detecting distance is increased, the output signal of the first light receiving unit 47 becomes "0" at a small turbidity, thereby narrowing the available range for detecting turbidity. In consideration of this concept, even if the first light emitting unit 47 emits light of the blue visible light range, the detecting distance of the turbidity sensor 40 is desired to be set to about 10 mm, that is, the distance between the first light emitting unit 41 and the first light receiving unit 47 is desired to be set to about 10 mm.

However, such a detecting distance of the turbidity sensor 40 may vary with a wavelength of light being emitted by the first light emitting unit 41 and a product to which the turbidity sensor 40 is applied.

Figure 8:
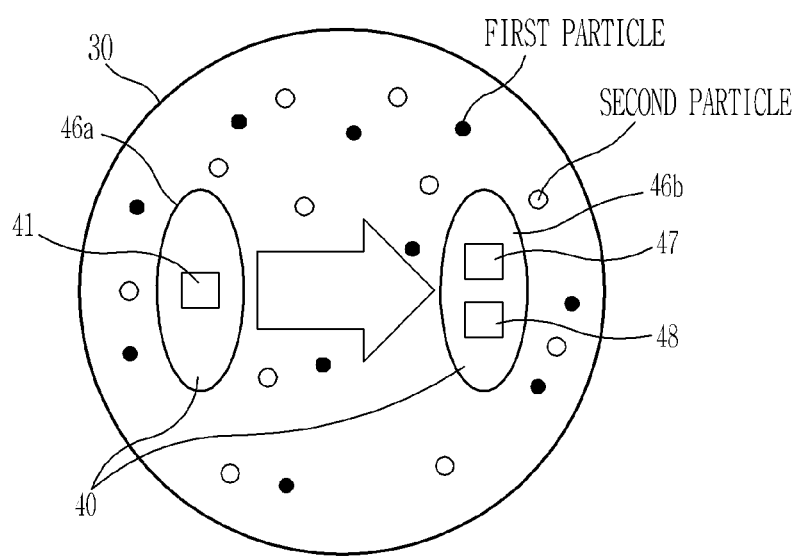
FIG. 8 is a conceptual view illustrating a turbidity sensor according to one embodiment.

FIG. 8 is a conceptual view illustrating a turbidity sensor 40 according to one embodiment. Some elements of FIG. 8, which are substantially the same as those of FIG. 4A, are denoted by the same reference numerals even though they are depicted in different drawings, and a detailed description thereof will thus be omitted.

Differently from the turbidity sensor 40 of FIG. 4A, the turbidity sensor 40 of FIG. 8 includes a first light emitting unit 41 simultaneously emitting visible light and infrared light. The turbidity sensor 40 of FIG. 8 further includes a second light receiving unit 48, in addition to the components of the turbidity sensor 40 of FIG. 4A. That is, the turbidity sensor 40 includes two light receiving units, namely, the first and second light receiving units, 47 and 48. The first light receiving unit 47 may receive visible light, and the second light receiving unit 48 may receive infrared light.

In FIG. 8, the second light receiving unit 48 may be disposed in parallel with the first light receiving unit 47 on a substrate 44 disposed below the first light emitting unit 41 and the first light receiving unit 47.

Thus, when the first light emitting unit 41 simultaneously emits visible light and infrared light at predetermined intensities, the first light receiving unit 47 receives visible light, which passes through water contained in a container 30 and travels straight, and the second light receiving unit 48 receives infrared light, which passes through water contained in a container 30 and travels straight.

The sensor control unit 45 according to the embodiment illustrated in FIG. 8 may determine turbidity of a solution measured using visible light by use of the amount of visible light emitted from the first light emitting unit 41 and the amount of visible light received by the first light receiving unit 47.

The sensor control unit 45 according to the embodiment illustrated in FIG. 8 may determine turbidity of a solution measured using infrared light by use of the amount of infrared light emitted from the first light emitting unit 41 and the amount of infrared light received by the second light receiving unit 48.

Thus, according to the embodiment illustrated in FIG. 8, turbidity of the solution may be measured using visible light as well as infrared light by use of the amount of light emitted from the first light emitting unit 41 and the amount of light received by the first and second light receiving units 47 and 48.

Figure 9:
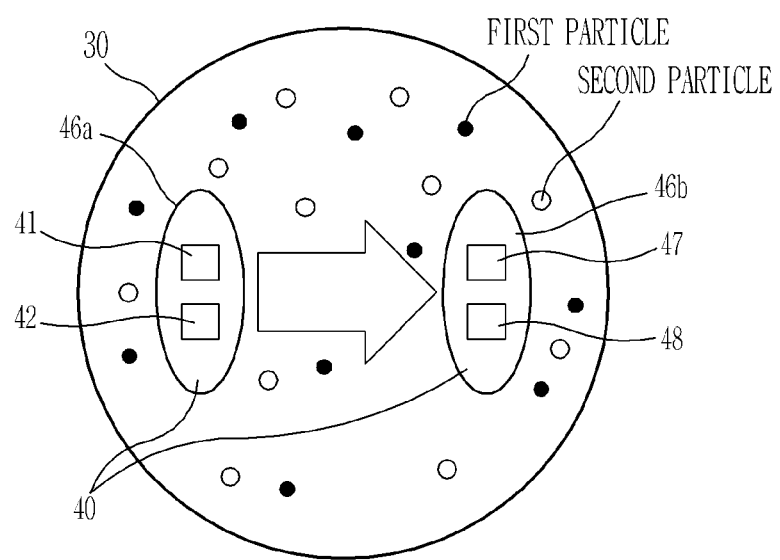
FIG. 9 is a conceptual view illustrating a turbidity sensor according to one embodiment.

FIG. 9 is a conceptual view illustrating a turbidity sensor 40 according to one embodiment of. Some elements of FIG. 9, which are substantially the same as those of FIG. 4A, are denoted by the same reference numerals even though they are depicted in different drawings, and a detailed description thereof will thus be omitted.

The turbidity sensor 40 of FIG. 9 further includes a second light emitting unit 42 and a second light receiving unit 48 in addition to the components of the turbidity sensor 40 of FIG. 4A. That is, the turbidity sensor 40 includes two light emitting units, namely, first and second light emitting units 41 and 42 and two light receiving units, namely, first and second light receiving units 47 and 48. In this regard, the first light emitting unit 41 may emit visible light, and the second light emitting unit 42 may emit infrared light. The first light receiving unit 47 may receive visible light, and the second light receiving unit 48 may receive infrared light.

In FIG. 9, the second light emitting unit 42 may be disposed in parallel with the first light emitting unit 41 on a substrate 44 disposed below the first light emitting unit 41 and the first light receiving unit 47. In addition, the second light receiving unit 48 may be disposed in parallel with the first light receiving unit 47 on the substrate 44 disposed below the first light emitting unit 41 and the first light receiving unit 47.

Thus, when the first light emitting unit 41 emits visible light at a predetermined intensity, the first light receiving unit 47 receives visible light, which passes through water contained in a container 30 and travels straight. When the second light emitting unit 42 emits infrared light at a predetermined intensity, the second light receiving unit 48 receives infrared light, which passes through water contained in the container 30 and travels straight.

The sensor control unit 45 according to the embodiment illustrated in FIG. 9 may determine turbidity of a solution measured using visible light by use of the amount of visible light emitted from the first light emitting unit 41 and the amount of visible light received by the first light receiving unit 47.

The sensor control unit 45 according to the embodiment illustrated in FIG. 9 may determine turbidity of a solution measured using infrared light by use of the amount of infrared light emitted from the second light emitting unit 42 and the amount of infrared light received by the second light receiving unit 48.

Thus, according to the embodiment illustrated in FIG. 9, turbidity of the solution measured using visible light and turbidity of the solution measured using infrared light may be determined by use of the amount of light emitted from the first and second light emitting units 41 and 42 and the amount of light received by the first and second light receiving units 47 and 48.

Figure 10A:
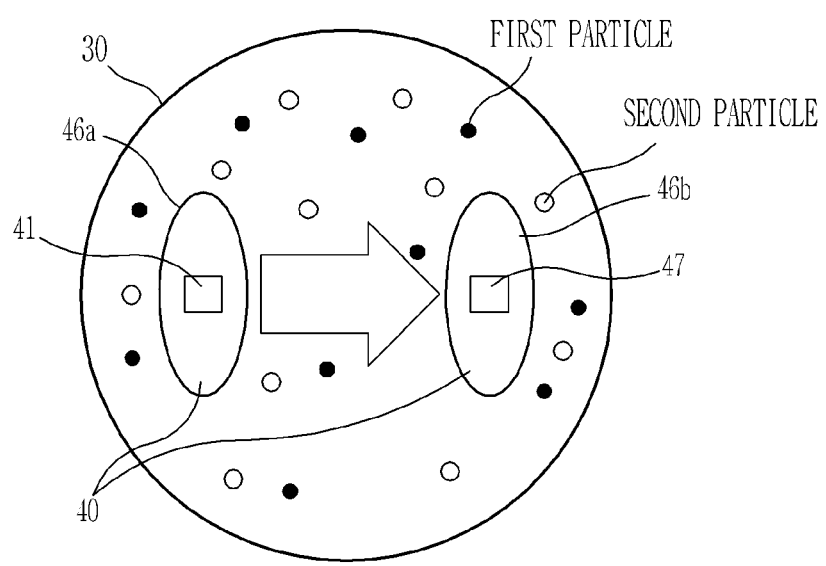
FIG. 10A is a conceptual view illustrating a turbidity sensor according to one embodiment.

FIG. 10A is a conceptual view illustrating a turbidity sensor 40 according to one embodiment. Some elements of FIG. 10A, which are substantially the same as those of FIG. 4A, are denoted by the same reference numerals even though they are depicted in different drawings, and a detailed description thereof will thus be omitted.

A first light emitting unit 41 may simultaneously emit visible light and infrared light, and the first light receiving unit 47 may simultaneously receive visible light and infrared light.

Thus, when the first light emitting unit 41 simultaneously emits visible light and infrared light at predetermined intensities, the first light receiving unit 47 receives visible light and infrared light, which passes through water contained in a container 30 and travels straight.

A sensor control unit 45 according to the embodiment illustrated in FIG. 10A may determine turbidity of a solution measured using visible light by use of the amount of visible light emitted from the first light emitting unit 41 and the amount of visible light received by the first light receiving unit 47.

The sensor control unit 45 according to the embodiment illustrated in FIG. 10A may determine turbidity of a solution measured using infrared light by use of the amount of infrared light emitted from the first light emitting unit 41 and the amount of infrared light received by the first light receiving unit 47.

Thus, according to the embodiment illustrated in FIG. 10A, turbidity of the solution measured using visible light and turbidity of the solution measured using infrared light may be determined by use of the amount of light emitted from the first light emitting unit 41 and the amount of light received by the first light receiving unit 47.

Figure 10B:
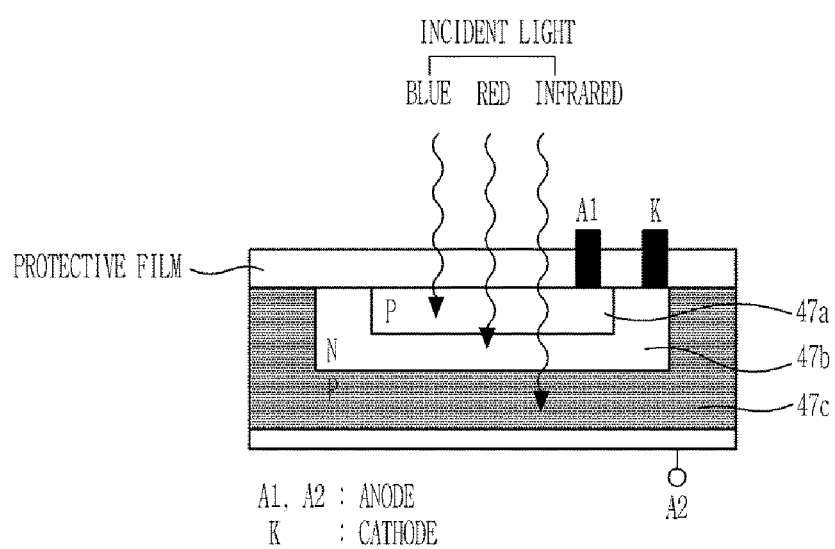
FIG. 10B is a view illustrating a first light receiving unit according to the embodiment illustrated in FIG. 10A.
Figure 10C:
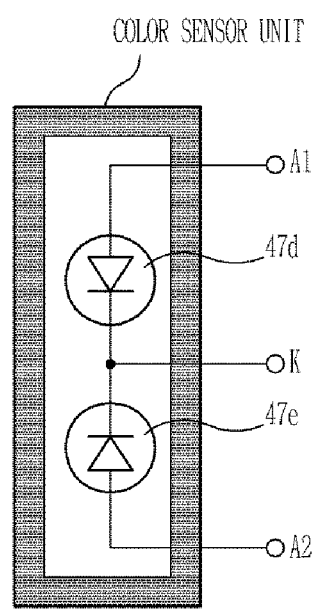
FIG. 10C is an equivalent circuit diagram of the first light receiving unit of the embodiment illustrated in FIG. 10A.

FIG. 10B is a view illustrating a first light receiving unit according to the embodiment illustrated in FIG. 10A. FIG. 10C is an equivalent circuit diagram of the first light receiving unit according to the embodiment illustrated in FIG. 10A.

Referring to FIGS. 10B and 9C, the first light receiving unit 47 is a multilayer photo diode having a p-type first region 47c, an n-type second region 47b, and a p-type third region 47a. A visible light receiving unit 47d may be formed of a PN junction between the third region 47a and the second region 47b, and an infrared light receiving unit 47e may be formed of a PN junction between the first region 47c and the second region 47b.

In this regard, wavelength ranges of light received by the visible light receiving unit 47d and the infrared light receiving unit 47e may be controlled by adjusting concentrations of impurities constituting each of the PN junctions.

Figure 10D:
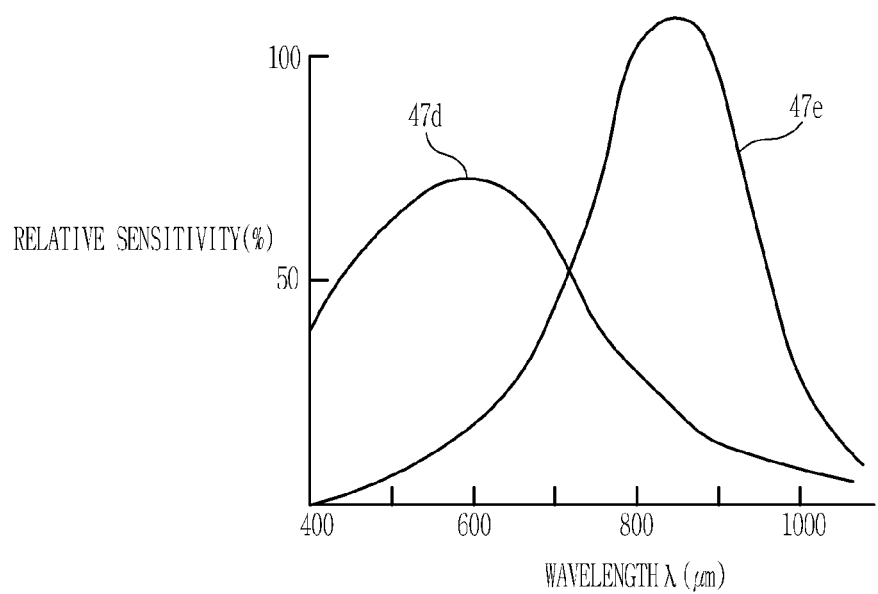
FIG. 10D is a graph illustrating relative sensitivity with respect to wavelength of light according to the embodiment illustrated in FIG. 10A.

FIG. 10D is a graph illustrating relative sensitivity with respect to wavelength of light according to the embodiment illustrated in FIG. 10A.

The visible light receiving unit 47d has a higher relative sensitivity to a wavelength range of visible light, thereby efficiently receiving visible light. The infrared light receiving unit 47e has a higher relative sensitivity to a wavelength range of infrared light, thereby efficiently receiving infrared light.

As such, the first light receiving unit 47 may simultaneously receive visible light and infrared light. The first light receiving unit 47 may be formed of at least two PN junctions, and the wavelength range of light received by the first light receiving unit 47 may be controlled by adjusting concentrations of impurities constituting each of the PN junctions. The first light receiving unit 47 may also be modified in a manner different from those described with reference to FIGS. 10B to 10D.

In addition, the first light emitting unit 41 may simultaneously emit visible light and infrared light. The first light emitting unit 41 may be formed of at least two PN junctions, and the wavelength range of light emitted therefrom may be controlled by adjusting concentrations of impurities constituting each of the PN junctions.

A sensor control unit 45 according to the embodiment illustrated in FIG. 10A may determine turbidity of a solution measured using visible light and turbidity of the solution measured using infrared light by use of the amount of light received by the visible light receiving unit 47d and the amount of light received by the infrared light receiving unit 47e.

Figure 11:
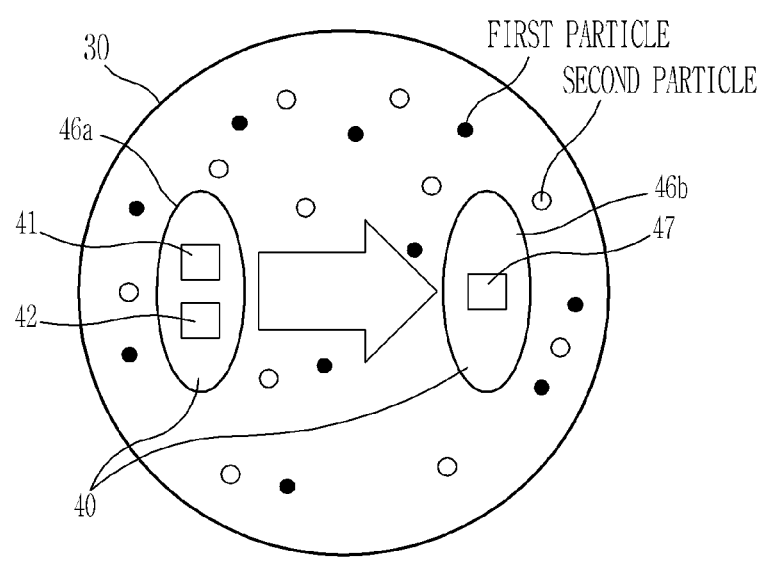
FIG. 11 is a conceptual view of a turbidity sensor according to one embodiment.

FIG. 11 is a conceptual view illustrating a turbidity sensor 40 according to one embodiment. Some elements of FIG. 11, which are substantially the same as those of FIG. 4A, are denoted by the same reference numerals even though they are depicted in different drawings, and a detailed description thereof will thus be omitted.

The turbidity sensor 40 of FIG. 11 further includes a second light emitting unit 42 in addition to the components of the turbidity sensor 40 of FIG. 4A. In this regard, a first light emitting unit 41 may emit visible light, and the second light emitting unit 42 may emit infrared light. A first light receiving unit 47 may simultaneously receive visible light and infrared light.

Thus, when the first and second light emitting units 41 and 42 simultaneously emit visible light and infrared light at predetermined intensities, the first light receiving unit 47 receives visible light and infrared light, which pass through water contained in a container 30 and travel straight.

A sensor control unit 45 according to the embodiment illustrated in FIG. 11 may determine turbidity of a solution measured using visible light by use of the amount of visible light emitted from the first light emitting unit 41 and the amount of visible light received by the first light receiving unit 47.

The sensor control unit 45 according to the embodiment illustrated in FIG. 11 may determine turbidity of a solution measured using infrared light by use of the amount of infrared light emitted from the second light emitting unit 42 and the amount of infrared light received by the first light receiving unit 47.

Thus, according to the embodiment illustrated in FIG. 11, turbidity of the solution measured using visible light and turbidity of the solution measured using infrared light may be determined by use of the amount of light emitted from the first and second light emitting units 41 and 42 and the amount of light received by the first light receiving unit 47.

Figure 12:
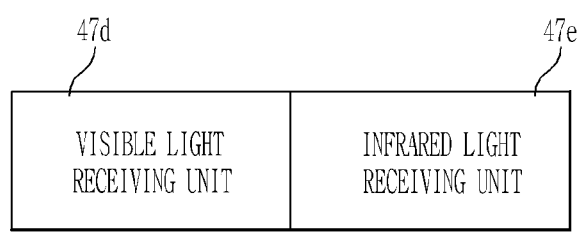
FIG. 12 is a view illustrating a structure of a first light receiving unit according to one embodiment.

FIG. 12 is a view illustrating a structure of a first light receiving unit according to one embodiment.

Referring to FIG. 12, a visible light receiving unit 47d and an infrared light receiving unit 47e of a first light receiving unit 47 may constitute a horizontal structure.

According to embodiments, the sensor control unit 45 may determine whether a detergent used in a solution is a powdered detergent or a liquid detergent. In addition, the sensor control unit 45 may also determine whether a pollutant contained in the solution is a liquid pollutant or a solid pollutant. The sensor control unit 45 may set a reference for measurement of turbidity.

TABLE 2

| Visible light | high | high | low |
|---|---|---|---|
| Infrared light | high | low | low |
| Particles | first particles and second particles | second particles | — |
| Type of detergent | powdered detergent | liquid detergent | — |
| Type of pollutant | solid pollutant | solid pollutant | — |

Referring to Table 2, when turbidity of a solution measured using visible light is greater than a first reference value, it is considered that the turbidity caused by first particles or second particles is high. When the turbidity of the solution measured using infrared light is greater than a second reference value, it is considered that the turbidity caused by the first particles is high. Accordingly, in this case, the sensor control unit 45 may determine that the first and second particles are contained in the solution, and the detergent contained in the solution is a powdered detergent. Or, the sensor control unit 45 may determine that a solid pollutant is contained in the solution. In addition, the sensor control unit 45 determines turbidity of the solution based on turbidity of the solution measured using infrared light.

When turbidity of the solution measured using visible light is greater than the first reference value, it is considered that the turbidity caused by first particles or second particles is high. When turbidity of the solution measured using infrared light is less than the second reference value, it is considered that the turbidity caused by the first particles is low. Accordingly, in this case, the sensor control unit 45 may determine that a large amount of the second particles is contained in the solution, and the detergent contained in the solution is a liquid detergent. Or, the sensor control unit 45 may determine that a liquid pollutant is contained in the solution. In addition, the sensor control unit 45 determines turbidity of the solution based on turbidity of the solution measured using visible light.

When turbidity of the solution measured using visible light is less than the first reference value, and turbidity of the solution measured using infrared light is less than the second reference value, the sensor control unit 45 may determine that the solution is clean. When turbidity of the solution measured using visible light is less than the first reference value, the sensor control unit 45 may also determine that the solution is clean.

In this regard, the first and second reference values may be obtained through experimentation and may vary.

Figure 13:
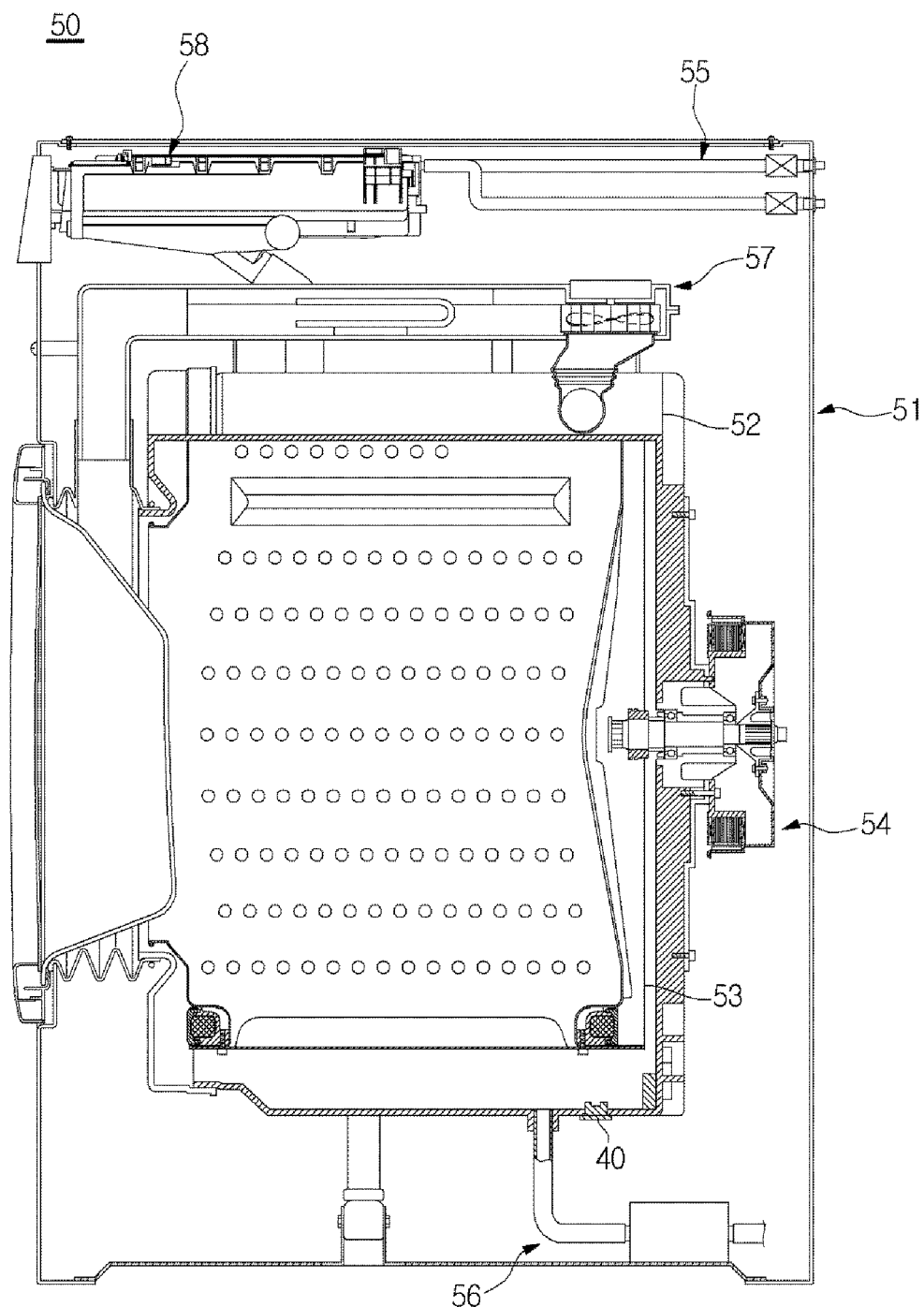
FIG. 13 is a view illustrating a washing machine including the turbidity sensor according to an embodiment.
Figure 14A:
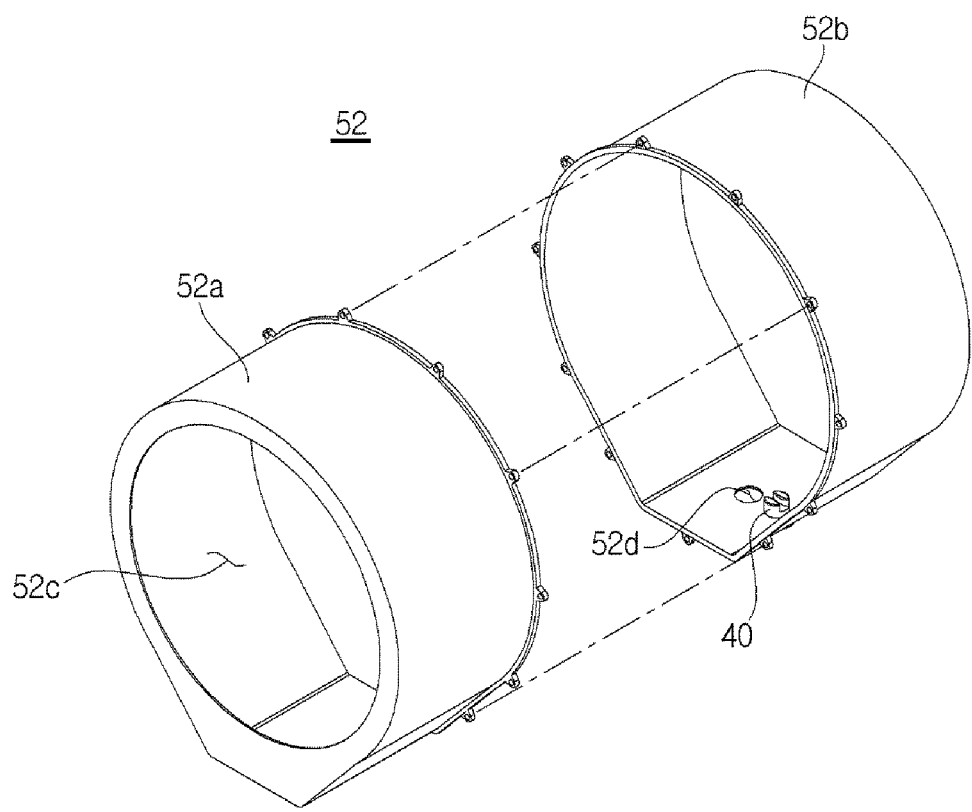
FIGS. 14A to 14C are views illustrating a tub of the washing machine including the turbidity sensor according to an embodiment.
Figure 14B:
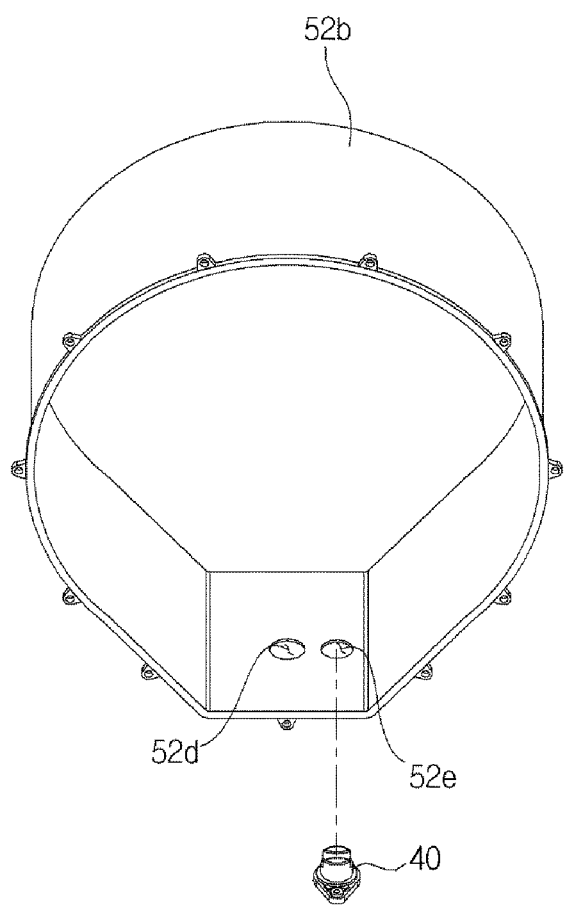
Figure 14C:
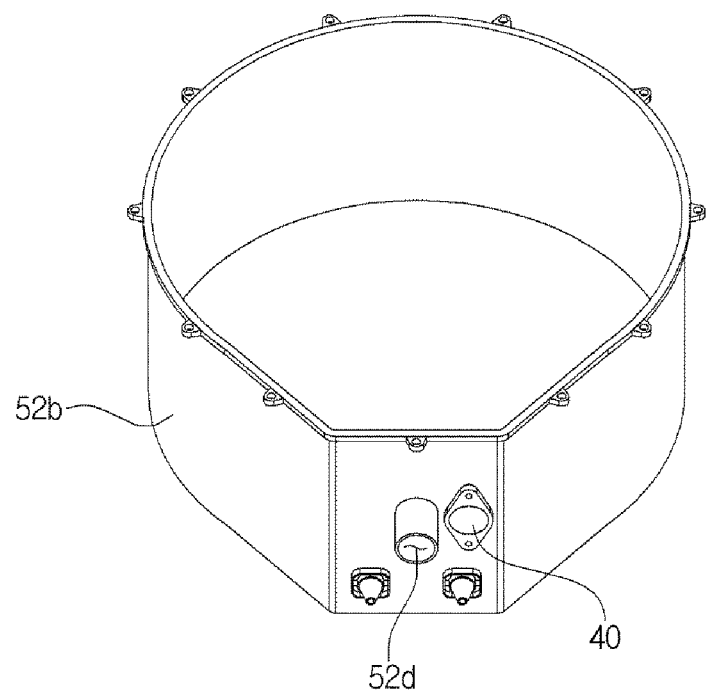

FIG. 13 is a view illustrating a washing machine including the turbidity sensor according to an embodiment, and FIGS. 14A to 14C are views illustrating a tub of the washing machine including the turbidity sensor according to an embodiment, Referring to FIG. 13 and FIGS. 14A to 14C, a washing machine 50 includes a body 51 forming the external appearance of the washing machine 50, a tub 52 containing wash water, a drum 53 rotatably provided at an inside the tub 52 to wash a laundry, a motor 54 rotating the drum 53, a water supply unit 56 supplying wash water to the tub 52, a drainage unit 56 draining wash water of the tub 52, a dry unit 57 drying the laundry at in inside the drum 53 after wash, a detergent supply unit 58 supplying detergent to the drum 53, and the turbidity sensor 40 detecting the turbidity of the wash water.

The tub 52 is provided at an inner side of the body 51, and formed by coupling a front surface member 52a to a rear surface member 52b. In addition, an opening 52c is formed at a front surface of the tub 52 such that a user puts in or takes out the laundry through the opening 52c. A drain port 52d is provided at a lower side of the tub 52 to discharge the wash water accommodated in the tub 52. In addition, a coupling hole 52e is provided at a position adjacent to the drain port 52d such that the turbidity sensor 40 is coupled to the coupling hole 52e.

The turbidity sensor 40 is coupled to the tub 52 through the coupling hole 52e provided at the tub 52. In this case, the turbidity sensor 40 is coupled such that the first light emitting unit 41 and the first light receiving unit 47 are disposed at a front side and a rear side of the turbidity sensor 40, respectively. That is, since the wash water turning together with the drum 53 when the drum 53 rotates is made to pass through between the first light emitting unit 41 and the first light receiving unit 47, the turbidity sensor 40 does not disturb the turning of the wash water. In addition, the turbidity sensor 40 may detect the turbidity not only at a limited certain area of the wash water but all areas of the wash water accommodated in the drum 53.

In addition, since the turbidity sensor 40 is provided at a lower side of the tub 52, the calibration of the turbidity sensor 40 is performed by use of clean water not containing contamination materials at the time of supplying wash water.

Figure 15A:
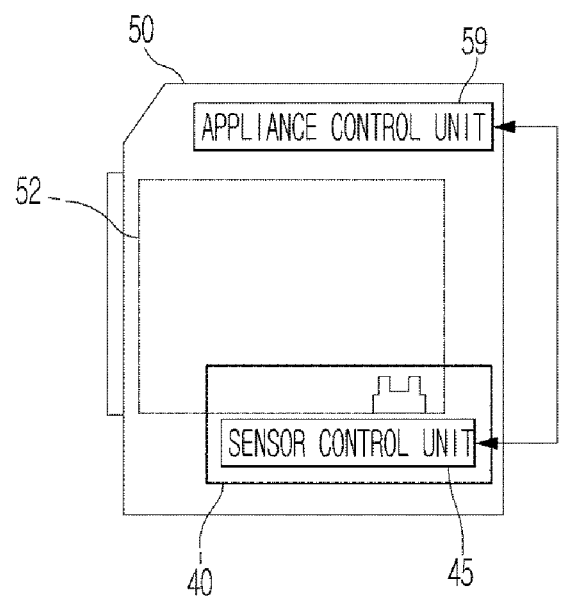
FIG. 15A is a view illustrating a control flow of the washing machine including the turbidity sensor according to an embodiment.
Figure 15B:
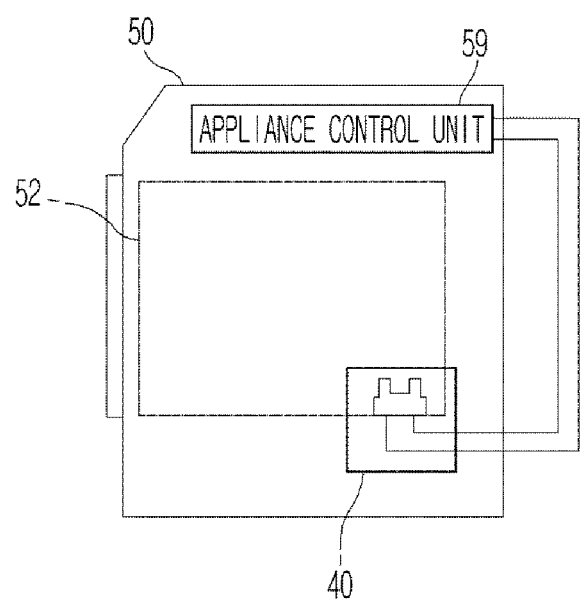
FIG. 15B is a view illustrating a control flow of the washing machine including the turbidity sensor according to an embodiment.

FIG. 15A is a view illustrating a control flow of the washing machine including the turbidity sensor according to an embodiment, and FIG. 15B is a view illustrating a control flow of the washing machine including the turbidity sensor according to an embodiment.

In FIGS. 15A and 15B, a tub 52 containing water for performing a washing/rinsing operation is installed in the washing machine 50, a turbidity sensor 40 for measuring the turbidity of the water contained in the tub 52 is installed at a lower portion in the tub 52, and an appliance control unit 59 for receiving the turbidity measured by the turbidity sensor 40 and then changing the washing/rinsing operation of the washing machine 50 is installed at a designated position in the washing machine 50.

The turbidity sensor 40 of FIG. 15A includes a sensor control unit 45 that measures a turbidity value using a ratio of the amount of light emitted from the first light emitting unit 41 and the amount of light received by the first light receiving unit 47, and transmits the measured turbidity value to the appliance control unit 59.

Then, the appliance control unit 54 of FIG. 15A receives the measured turbidity value from the sensor control unit 45 of the turbidity sensor 40, and additionally performs the washing/rinsing operation, when the measured turbidity value is a reference turbidity or greater, or terminates the washing/rinsing operation, when the measured turbidity value is less than the reference turbidity.

On the other hand, the turbidity sensor 40 of FIG. 15B may have a circuit that transmits output values of the amount of light emitted from the first light emitting unit 41 and the amount of light received by the first light receiving unit 47 to the appliance control unit 54 without having the sensor control unit 45.

Thus, the appliance control unit 54 of FIG. 15B directly receives the amount of light emitted from the first light emitting unit 41 of the turbidity sensor 40 and the amount of light received by the first light receiving unit 47, calculates a ratio of the amounts, and determines the turbidity. The appliance control unit 54 additionally performs the washing/rinsing operation, when the measured turbidity value is the reference turbidity or greater, and terminates the washing/rinsing operation, when the measured turbidity value is less than the reference turbidity.

Figure 16:
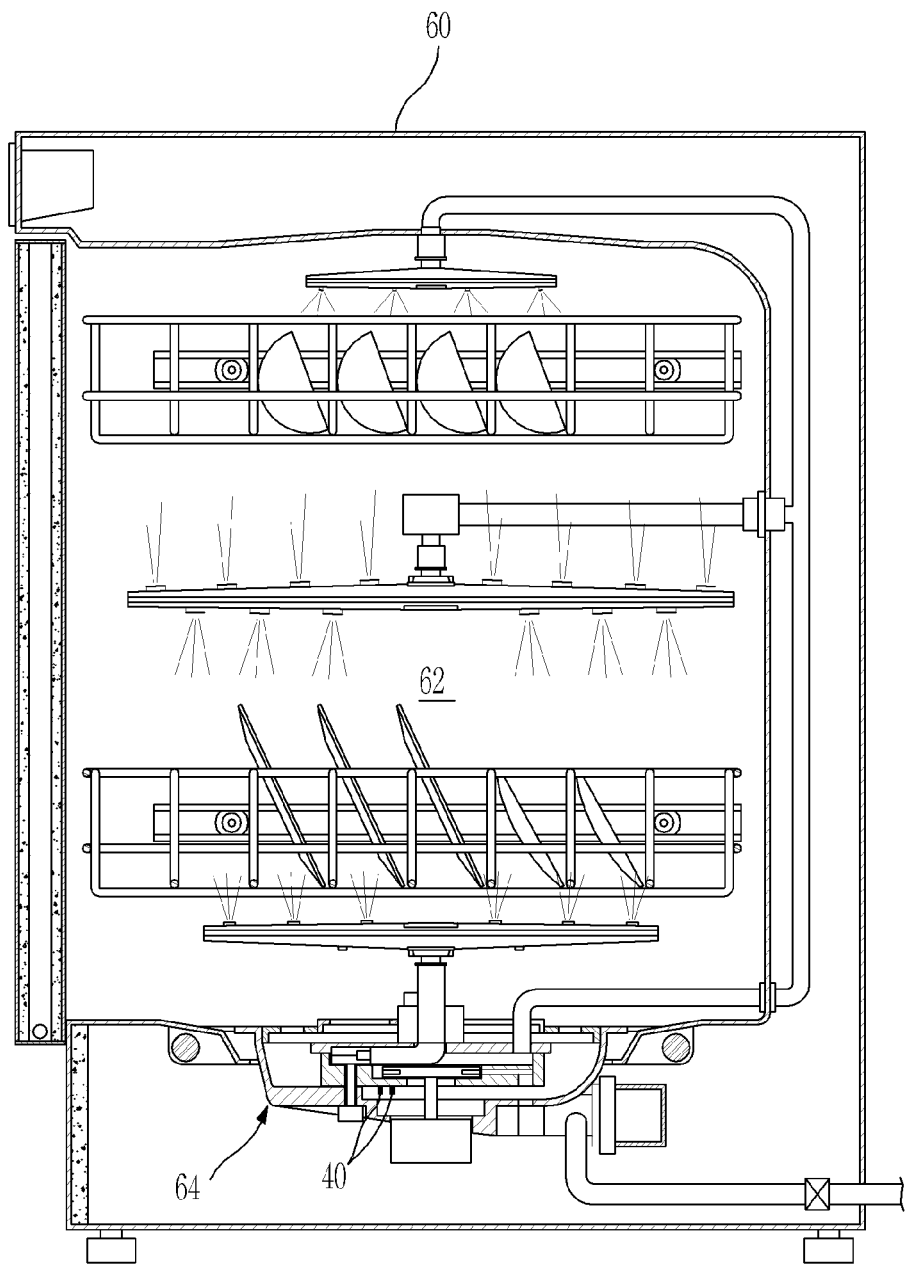
FIG. 16 is a schematic view illustrating an example of installation of the turbidity sensor according to the embodiment illustrated in FIG. 3A in a dishwasher.

FIG. 16 is a schematic view illustrating an example of installation of the turbidity sensor according to the embodiment illustrated in FIG. 3A in a dishwasher. The description of the whole structure of a dishwasher 60 will be omitted, and the structure of a portion of the dishwasher 60, in which a turbidity sensor 40 is installed, will be described in detail.

In FIG. 16, a washing tub 62 for performing a washing/rinsing operation is provided in the dishwasher 60. A sump 64 for collecting water supplied to the inside of the washing tub 62 and pumping out the water is provided under the washing tub 62. The turbidity sensor 40 for measuring the turbidity of the water is installed in the sump 64.

Figure 17:
FIG. 17 is a control block diagram of the dishwasher, in which the turbidity sensor according to the embodiment illustrated in FIG. 3A is installed.

FIG. 17 is a control block diagram of the dishwasher, in which the turbidity sensor according to the embodiment illustrated in FIG. 3A is installed. The dishwasher 60 includes the turbidity sensor 40, an appliance control unit 66, and a driving unit 68.

The fundamental operation of the appliance control unit 66 in connection with the measurement of turbidity by the turbidity sensor 40 is similar to that of the appliance control unit 54 of the washing machine 50 of FIG. 12 or 13. However, the appliance control unit 66 is different from the appliance control unit 54 in that the appliance control unit 66 of the dishwasher 60 has an algorithm, which is implemented so as to satisfy the operation of the dishwasher, such that a washing/rinsing operation is additionally performed when the measured turbidity is a reference turbidity or greater, and the washing/rinsing operation is terminated when the measured turbidity is less than the reference turbidity. Accordingly, an optimal washing/rinsing operation may be performed without wasting water.

That is, the appliance control unit 66 may receive the turbidity value measured by the sensor control unit 45 of the turbidity sensor 40 and then change the washing/rinsing operation. Alternatively, the appliance control unit 66 may receive the amount of light emitted from the first light emitting unit 41 of the turbidity sensor 40 and the amount of light received by the first light receiving unit 47, calculate a ratio of the amounts of light, and then determine the turbidity of water.

The driving unit 68 drives a load of the dishwasher 60 according to a driving control signal of the appliance control unit 66.

The control block diagram of the dishwasher including the turbidity sensor as shown in FIG. 17 may also be applied to washing machines and other electric home appliances including the turbidity sensor in a similar manner.

Hereinafter, operations and functions of the above turbidity sensor and an electric home appliance including the same will be described.

Figure 18:
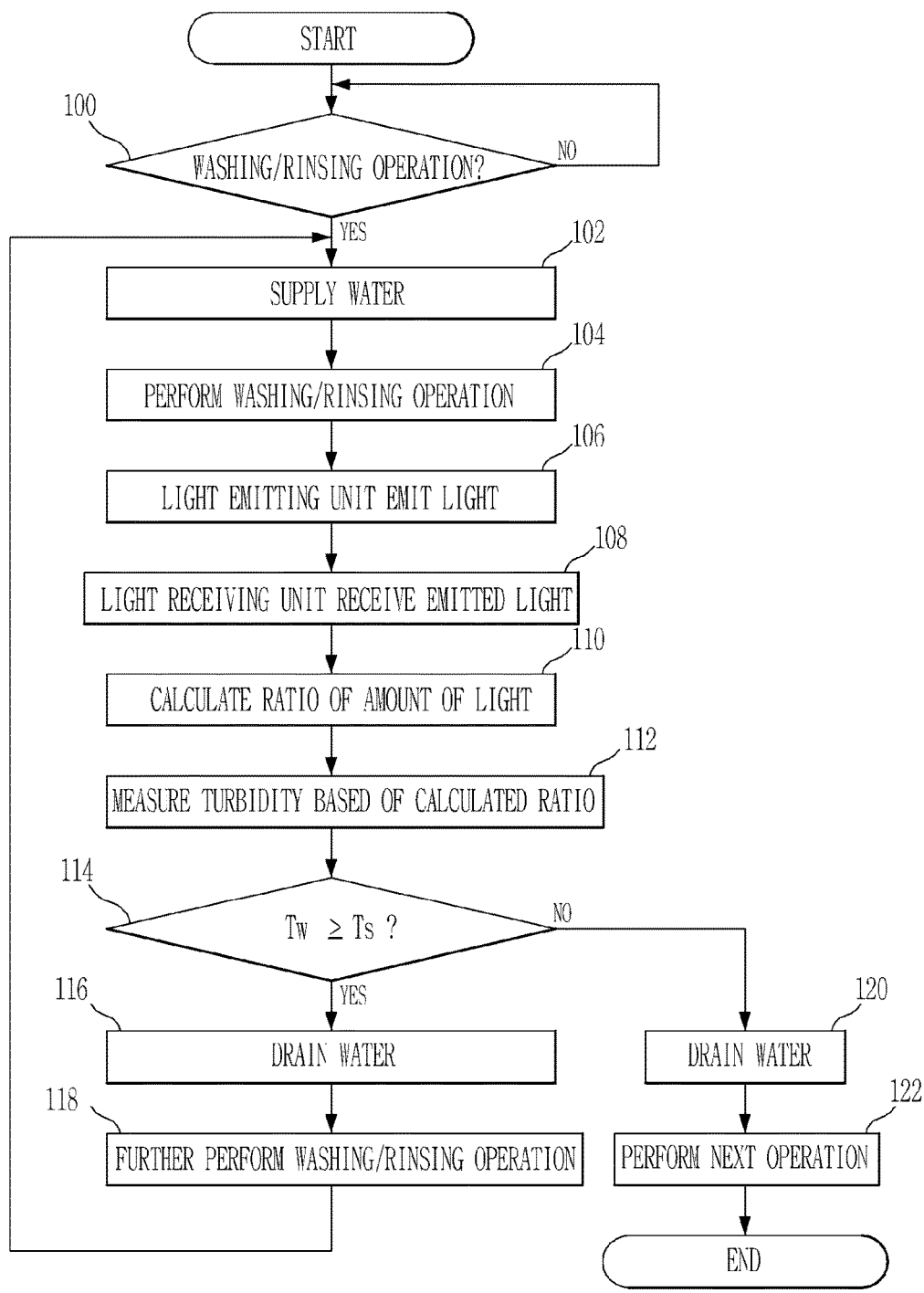
FIG. 18 is a flowchart illustrating a method of measuring turbidity in the dishwasher, in which the turbidity sensor according to the embodiment illustrated in FIG. 3A is installed.

FIG. 18 is a flowchart illustrating a method of measuring turbidity in the dishwasher, in which the turbidity sensor according to the embodiment illustrated in FIG. 3A is installed.

The appliance control unit 66 determines whether or not a washing/rinsing operation is started under the condition that dishes to be washed are put in the washing tub 62 (100), and supplies water required to perform the washing/rinsing operation to the inside of the washing tub 62 through the driving unit 68, when it is determined that the washing/rinsing operation is started (102).

The water supplied to the inside of the washing tub 62 flows into the sump 64 provided under the washing tub 62, and then is sprayed onto the dishes in the washing tub 62 so as to perform the washing/rinsing operation (104).

When the washing/rinsing operation is performed, contaminants stuck to the dishes are washed off by the water and the water and contaminants are supplied to the sump 64. Thus, when the first light emitting unit 41 of the turbidity sensor 40 installed in the sump 64 emits visible light at a predetermined intensity so as to measure the turbidity of the water (106), the first light receiving unit 47 receives light, which passes through water in the sump 64 and travels straight and is scattered by particles contained in the water (108).

Thus, the sensor control unit 45 measures the turbidity (Tw) of water by calculating a ratio of the amount of light emitted from the first light emitting unit 41 to the amount of light received by the first light receiving unit 47 (110), and transmits the measured turbidity (Tw) to the appliance control unit 66 (112).

Then, the appliance control unit 66 compares the turbidity (Tw) of the water measured by the sensor control unit 45 of the turbidity sensor 40 with a reference turbidity (Ts) (114). When the measured turbidity (Tw) is the reference turbidity (Ts) or greater, the water in the washing tub 62 is drained (116), and then the method is fed back to step 102 so as to additionally perform the washing/rinsing operation (118).

As a result of comparison in operation 114, when the measured turbidity (Tw) is less than the reference turbidity (Ts), it is determined that the washing/rinsing operation is completed and the water in the washing tub 62 is drained (120), and then a next operation is performed (122).

Although FIGS. 12 to 14 illustrate examples of installation of the turbidity sensor 40 according to embodiments in the washing machine 50 and the dishwasher 60, the turbidity sensor 40 is not limited thereto, but may be applied to any electric home appliances using water, such as a water purifier. In addition, in FIG. 18, a method of measuring turbidity using the turbidity sensor according to the embodiment illustrated in FIG. 3A is described. However, the disclosure is not limited thereto, and the method may also be applied to the other embodiments of the present invention in a similar manner.

Figure 19:
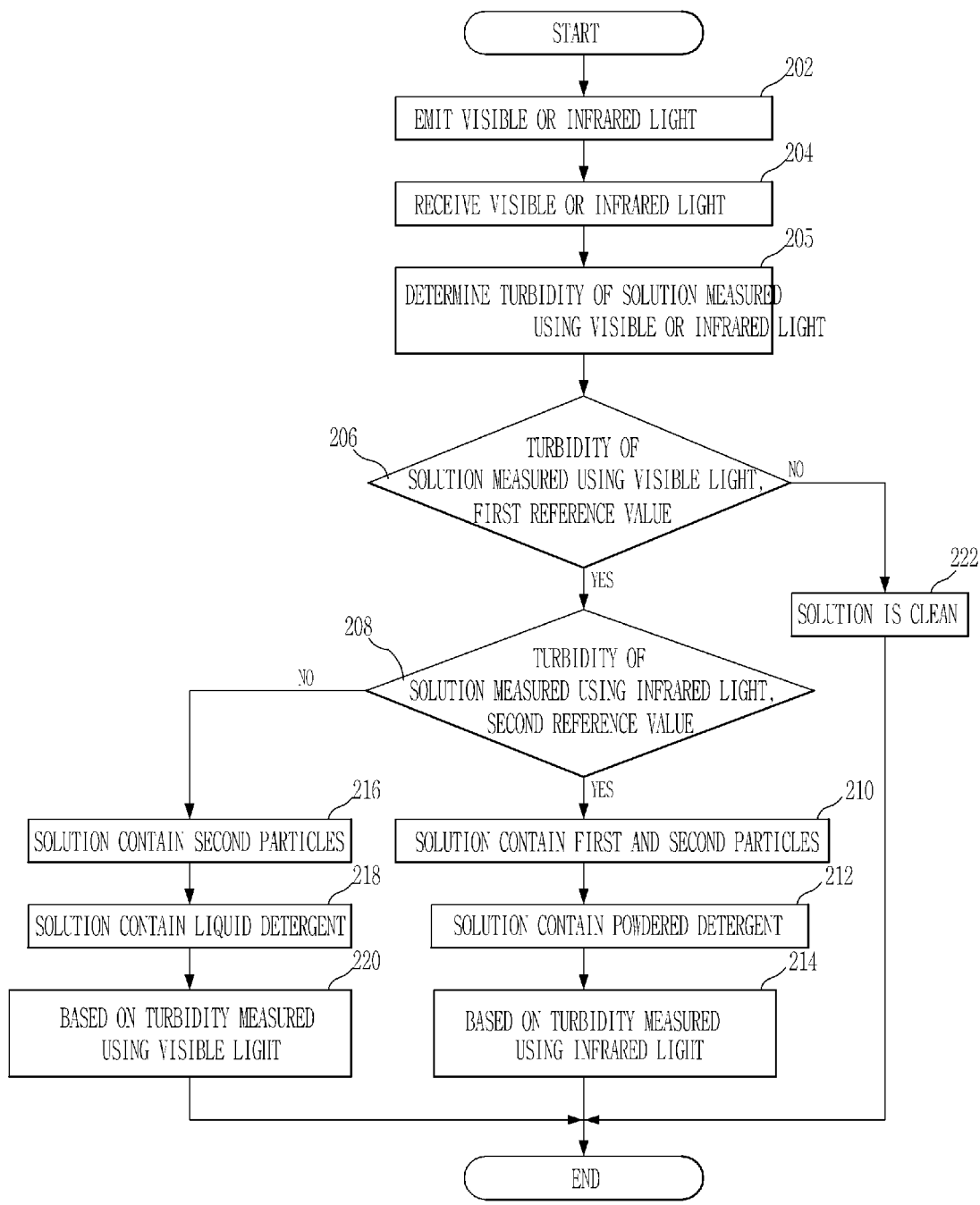
FIG. 19 is a flowchart illustrating a method of controlling turbidity sensors according to embodiments.

FIG. 19 is a flowchart illustrating a method of controlling turbidity sensors 40 according to embodiments. The method of controlling the turbidity sensor 40 may include characteristics described above with reference to FIGS. 3A to 16.

The first light emitting unit 40 according to the embodiment illustrated in FIG. 3A may emit visible light or infrared light (202). In this regard, visible light and infrared light may be simultaneously or sequentially emitted.

The turbidity sensor 40 may receive visible light or infrared light (204). In this regard, visible light and infrared light may be simultaneously or sequentially received.

The turbidity sensor 40 may determine turbidity of a solution measured using visible light according to a ratio of the amount of emitted visible light to the amount of received visible light, and determines turbidity of the solution measured using infrared light according to a ratio of the amount of emitted infrared light to the amount of received infrared light (205).

Then, the turbidity sensor 40 may determine whether a detergent used in the solution is a powdered detergent or a liquid detergent. The turbidity sensor 40 may also determine whether a pollutant contained in the solution is a liquid pollutant or a solid pollutant. The turbidity sensor 40 may set a reference value for measurement of turbidity.

When turbidity of the solution measured using visible light is greater than a first reference value, it is considered that the turbidity caused by first particles or second particles is high. When turbidity of the solution measured using infrared light is greater than a second reference value, it is considered that the turbidity caused by the first particles is high. Accordingly, in this case, the turbidity sensor 40 may determine that both the first and second particles are contained in the solution, and the detergent contained in the solution is a powdered detergent. Or, the turbidity sensor 40 may determine that a solid pollutant is contained in the solution. In addition, the turbidity sensor 40 determines turbidity of the solution based on turbidity of the solution measured using infrared light (206, 208, 210, 121, and 214).

When turbidity of the solution measured using visible light is greater than the first reference value, the turbidity sensor 40 may determine that the turbidity caused by first particles or second particles is high. When turbidity of the solution measured using infrared light is less than the second reference value, the turbidity sensor 40 may determine that the turbidity caused by the first particles is low. Accordingly, in this case, the turbidity sensor 40 may determine that a large amount of the second particles is contained in the solution, and the detergent contained in the solution is a liquid detergent. Or, the turbidity sensor 40 may determine that a liquid pollutant is contained in the solution. In addition, the turbidity sensor 40 determines turbidity of the solution based on turbidity of the solution measured using visible light (206, 208, 216, 118, and 220).

When turbidity of the solution measured using visible light is less than the first reference value, and turbidity of the solution measured using infrared light is less than the second reference value, the sensor control unit 40 may determine that the solution is clean. When turbidity of the solution measured using visible light is less than the first reference value, the sensor control unit 40 may also determine that the solution is clean (206, 208, and 222).

In this regard, the first and second reference values may be obtained through experimentation and may vary.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A home appliance for performing washing by using water and detergent, the home appliance comprising:
   a tub to accommodate a solution including the water and the detergent;
   a turbidity sensor mounted inside the tub and to detect a turbidity of the solution;
   wherein the turbidity sensor induces:
      a first light emitting unit emitting visible light and infrared light;
      a first light receiving unit receiving the visible light emitted and the infrared light from the first light emitting unit; and
      a control unit determining the turbidity of the solution according to a ratio between an amount of the visible light emitted from the first light emitting unit and an amount of the visible light received by the first light receiving unit,
   wherein the control unit determines if the solution includes one of a powder detergent and a liquid detergent based on comparing the amount of the visible light received by the first light receiving unit with a first reference value and comparing an amount of the infrared light received by the first light receiving unit with a second reference value, and
   wherein the control unit determines the turbidity of the solution containing the powder detergent based on measurements using the visible light but not based on measurements using the infrared light and the control unit determines the turbidity of the solution containing the liquid detergent based on measurements using the infrared light but not based on measurements using the visible light.

2. The home appliance according to claim 1, wherein:
the turbidity sensor further comprises a second light receiving unit disposed opposite to the first light emitting unit at a position spaced apart from the first light emitting unit and receiving the infrared light emitted from the first light emitting unit; and
the control unit determines the turbidity of the solution measured using the visible light according to the ratio between the amount of the visible light emitted from the first light emitting unit and the amount of the visible light received by the first light receiving unit and determines a turbidity of the solution measured using the infrared light according to a ratio between the amount of the infrared light emitted from the first light emitting unit and the amount of the infrared light received by the second light receiving unit.

3. The home appliance according to claim 2, wherein when a turbidity measured using the visible light is greater than the first reference value and a turbidity measured using the infrared light is greater than the second reference value, the sensor control unit determines that both of first and second particles are contained in the solution, determines that the detergent contained in the solution is the powdered detergent, and determines the turbidity of the solution based on the turbidity of the solution measured using the infrared light.

4. The home appliance according to claim 2, wherein when a turbidity measured using the visible light is greater than the first reference value and a turbidity measured using the infrared light is less than the second reference value, the sensor control unit determines that second particles are contained in the solution, determines that the detergent contained in the solution is the liquid detergent, and determines the turbidity of the solution based on the turbidity of the solution measured using the visible light.

5. The home appliance according to claim 2, wherein when a turbidity measured using the visible light is less than a first reference value, the sensor control unit determines that the solution is clean.

6. The home appliance according to claim 1, wherein:
the turbidity sensor further comprises a second light emitting unit emitting the infrared light and a second light receiving unit disposed opposite to the second light emitting unit at a position spaced apart from the second light emitting unit and receiving the infrared light emitted from the second light emitting unit; and
the control unit determines the turbidity of the solution measured using the visible light according to the ratio between the amount of the visible light emitted from the first light emitting unit and the amount of the visible light received by the first light receiving unit and determines a turbidity of the solution measured using the infrared light according to a ratio between the amount of the infrared light emitted from the second light emitting unit and the amount of the infrared light received by the second light receiving unit.

7. The home appliance according to claim 1, wherein:
the first light emitting unit further emits the infrared light;
the first light receiving unit further receives the infrared light emitted from the first light emitting unit; and
the control unit determines a turbidity of the solution measured using the visible light according to a ratio between the amount of the visible light emitted from the first light emitting unit and the amount of the visible light received by the first light receiving unit and determines a turbidity of the solution measured using the infrared light according to a ratio between the amount of the infrared light emitted from the first light emitting unit and the amount of the infrared light received by the first light receiving unit.

8. The home appliance according to claim 1, wherein:
the turbidity sensor further comprises a second light emitting unit emitting the infrared light;
the first light receiving unit further receives the infrared light emitted from the second light emitting unit; and
the control unit determines the turbidity of the solution measured using the visible light according to the ratio between the amount of the visible light emitted from the first light emitting unit and the amount of the visible light received by the first light receiving unit and determines a turbidity of the solution measured using the infrared light according to a ratio between the amount of the infrared light emitted from the second light emitting unit and the amount of the infrared light received by the first light receiving unit.

9. The home appliance according to claim 1, wherein the ratio is obtained by the amount of the visible light received by the first light receiving unit/the amount of the visible light emitted from the first light emitting unit.

10. The home appliance according to claim 1, further comprising:
a light emitting unit case allowing light emitted from the first light emitting unit to travel straight to the first light receiving unit; and
a light receiving unit case allowing light emitted from the first light emitting unit to be incident upon the first light receiving unit and blocking scattered light.

11. The home appliance according to claim 1, further comprising:
a light emitting unit cover surrounding the first light emitting unit to prevent the first light emitting unit from directly contacting the solution; and
a light receiving unit cover surrounding the first light receiving unit to prevent the first light receiving unit from directly contacting the solution.

12. The home appliance according to claim 1, wherein the visible light emitted by the first light emitting unit includes light having a blue color.

13. The home appliance according to claim 1, wherein the visible light emitted by the first light emitting unit includes light having a wavelength of about 460 nm.

14. The home appliance according to claim 1 wherein a distance between the first light emitting unit and the first light receiving unit is between 8 mm and 12 mm.

15. The home appliance according to claim 1 wherein a distance between the first light emitting unit and the first light receiving unit is about 10 mm.

* * * * *